US009292765B2

(12) United States Patent
Knee et al.

(10) Patent No.: US 9,292,765 B2
(45) Date of Patent: Mar. 22, 2016

(54) MAPPING GLINTS TO LIGHT SOURCES

(71) Applicant: Microsoft Technology Licensing, LLC, Redmond, WA (US)

(72) Inventors: Derek Knee, Fort Collins, CO (US); John Eldridge, Bellevue, WA (US); Robert Havlik, Fort Collins, CO (US); Ronald Boskovic, Issaquah, WA (US); Christopher Mei, Seattle, WA (US); Gerhard Schneider, Seattle, WA (US); Djordje Nijemcevic, Kragujevac (RS); David Nister, Bellevue, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 101 days.

(21) Appl. No.: 14/149,577

(22) Filed: Jan. 7, 2014

(65) Prior Publication Data

US 2015/0193920 A1    Jul. 9, 2015

(51) Int. Cl.
| | |
|---|---|
| G06K 9/00 | (2006.01) |
| G06K 9/62 | (2006.01) |
| H04N 5/243 | (2006.01) |
| A61B 3/113 | (2006.01) |
| G06F 3/01 | (2006.01) |
| G06T 7/00 | (2006.01) |

(52) U.S. Cl.
CPC ............. *G06K 9/6215* (2013.01); *A61B 3/113* (2013.01); *G06F 3/013* (2013.01); *G06T 7/0042* (2013.01); *H04N 5/243* (2013.01); *G06T 2207/10016* (2013.01); *G06T 2207/10152* (2013.01); *G06T 2207/20224* (2013.01)

(58) Field of Classification Search
None
See application file for complete search history.

(56) References Cited

U.S. PATENT DOCUMENTS 6,659,611 B2    12/2003  Amir et al.
8,971,570 B1 *   3/2015  Raffle .................... G02B 27/00
                                                    382/103

(Continued)

FOREIGN PATENT DOCUMENTS

| WO | 0026713 A1 | 5/2000 |
|---|---|---|
| WO | 2005052718 A2 | 6/2005 |
| WO | 2012055444 A1 | 5/2012 |

OTHER PUBLICATIONS

"ITU Gaze Tracker", A brief users guide, v1.0b, Gaze Group at the IT University of Copenhagen, supported by the Communication by Gaze Interaction association (COGAIN), Apr. 2009, Available at: http://www.gazegroup.org/downloads/23-gazetracker.

(Continued)

*Primary Examiner* — Jayesh A Patel
(74) *Attorney, Agent, or Firm* — Dan Choi; Judy Yee; Micky Minhas

(57) ABSTRACT

The technology disclosed herein provides various embodiments for mapping glints that reflect off from an object to light sources responsible for the glints. Embodiments disclosed herein are able to correctly map glints to light sources by capturing just a few images with a camera. Each image is captured while illuminating the object with a different pattern of light sources. A glint free image may also be determined. A glint free image is one in which the glints have been removed by image processing techniques.

18 Claims, 13 Drawing Sheets

(56) References Cited

U.S. PATENT DOCUMENTS

| | | | |
|---|---|---|---|
| 2002/0051116 A1* | 5/2002 | Van Saarloos | A61B 3/113 351/204 |
| 2006/0110008 A1 | 5/2006 | Vertegaal et al. | |
| 2008/0084499 A1* | 4/2008 | Kisacanin | A61B 3/113 348/370 |
| 2011/0228975 A1 | 9/2011 | Hennessey et al. | |
| 2012/0294478 A1 | 11/2012 | Publicover et al. | |
| 2013/0114850 A1 | 5/2013 | Publicover et al. | |

OTHER PUBLICATIONS

Villanueva, et al., "Geometry Issues of Gaze Estimation", Advances in Human-Computer Interaction, Shane Pinder (Ed.), ISBN: 978-953-7619-15-2, Oct. 2008, pp. 513-534, InTech, 23 pages.

"International Search Report and Written Opinion Issued in PCT Application No. PCT/US2014/072304", Mailed Date: Mar. 9, 2015, 12 Pages.

* cited by examiner

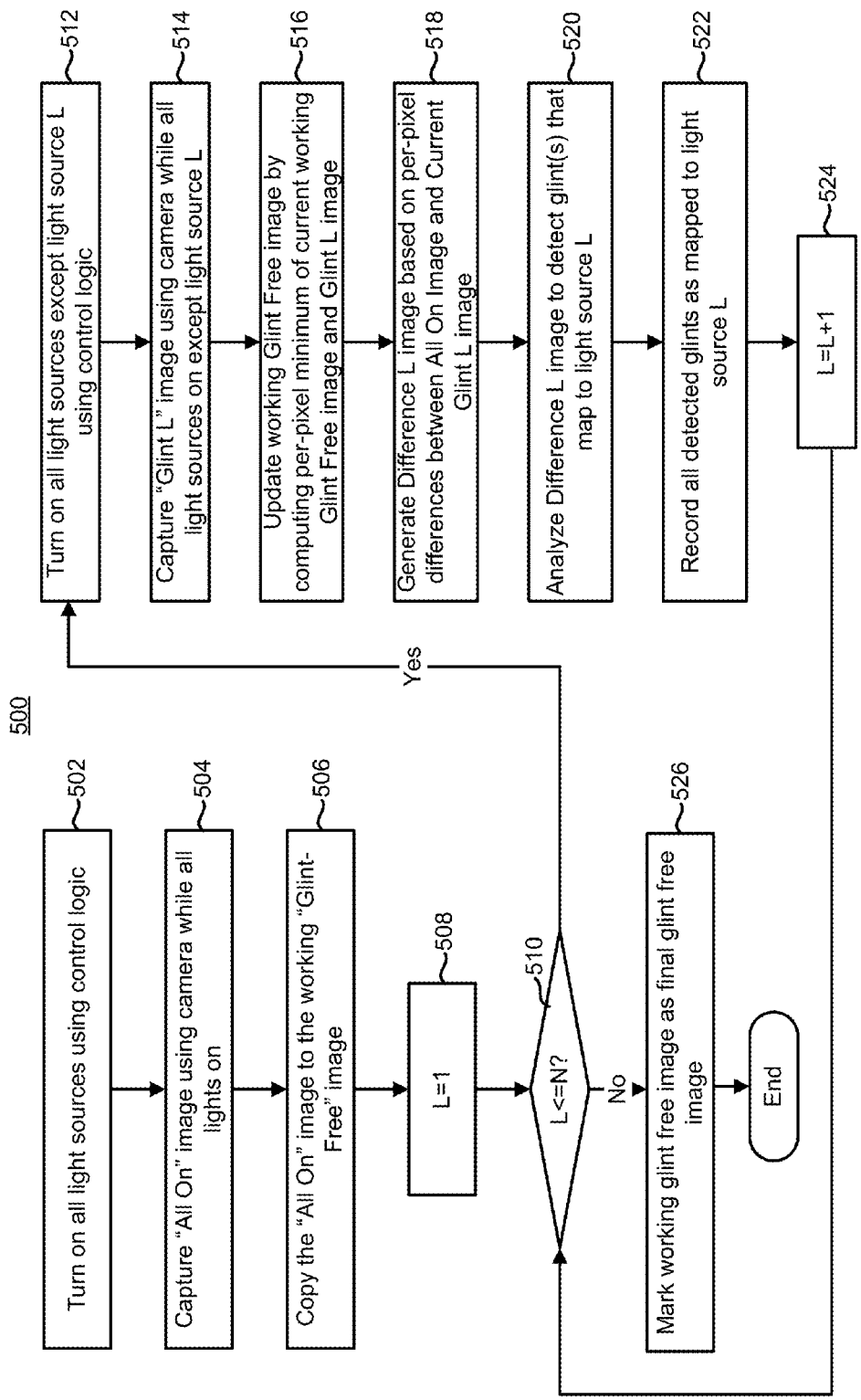

MAPPING GLINTS TO LIGHT SOURCES

BACKGROUND

A glint is the reflection of a light source off from an object. For example, when light from a light source reflects off from someone's eye, a glint can be detected in an image captured by a camera. The glints can be analyzed to perform such functions as determining 3D geometry of the object. If the object is a person's eye, it is possible to determine a 3D vector that describes a direction in which the person is gazing. There are many other applications of analyzing glints, such as object recognition, high speed motion tracking, and production line control.

SUMMARY

The technology provides various embodiments for mapping glints to light sources. A correct mapping of the glints to light sources responsible for the glint is useful in being able to perform such functions as determining 3D geometry of the object. A glint free image may also be determined. A glint free image is one in which the glints have been removed by image processing techniques. Having a glint free image can be useful in helping to identify elements of the object, such as the pupil of a person's eye.

One embodiment includes a method of mapping a glint to a light source, which comprises the following. An object is illuminated with patterns of light sources. The patterns include a first pattern in which a first light source of the light sources is on and a second pattern in which the first light source is off. Images of the object are captured at a camera while illuminating the object with corresponding ones of the patterns. Glints in the captured plurality of images are analyzed. Based on the analysis, a glint is mapped to the light source that is responsible for the glint.

One embodiment is a system comprising a plurality of light sources, a camera and logic in communication with the plurality of light source and the camera. The logic is configured to control the light sources to illuminate an object with patterns of a plurality of light sources. The patterns include a first pattern in which a first light source of the light sources is on and a second pattern in which the first light source is off. Each of the light sources is off for at least one of the patterns and on for at least one of the patterns. The logic is configured to capture images of the object at the camera while illuminating the object with corresponding different ones of the patterns. The logic is configured to analyze glints in the captured images as a result of illuminating the object with the patterns. The logic is configured to map a glint to the light source that is responsible for the glint based on the analysis.

One embodiment is a method comprising the following. An eye is illuminated with patterns of a plurality of light sources. The patterns include a first pattern in which a first light source of the light sources is on and a second pattern in which the first light source is off. Each of the light sources is off for at least one of the patterns and on for at least one of the patterns. Images of the eye are captured at a camera while illuminating the eye with corresponding ones of the patterns. Glints in the captured plurality of images are analyzed. Based on the analysis, the glints are mapped to the light source that is responsible for the respective glint. A direction of eye gaze is determined based on the glints.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 5 is a flowchart of one embodiment of a process of mapping glints to light sources and generating a glint free image that involves turning off one light source at a time.

DETAILED DESCRIPTION

The technology disclosed herein provides various embodiments for mapping glints that reflect off from an object to a light source responsible for the respective glint. A correct mapping of glints to respective light sources is useful in being able to perform such functions as determining 3D geometry of the object. It is possible to determine the 3D geometry from 2D images of the object. However, correctly mapping the glints to their respective light sources can be challenging. One challenge is that the object could be moving. As one example, a person's eye could be moving fairly rapidly. Therefore, it can be beneficial to have a technique that can be performed very rapidly to reduce problems associated with motion artifacts.

Embodiments disclosed herein are able to correctly map glints to light sources while capturing just a few images with a camera. Each image is captured while illuminating the object with a different pattern of light sources, in one embodiment. Further details are discussed below.

A glint free image may also be determined. A glint free image is one in which the glints have been removed by image processing techniques. Having a glint free image can be useful in helping to identify elements of the object. For example, the pupil of a person's eye can be more easily located with a glint free image. The glint free image can be determined from the same captured images that are used to map the glints to light sources, with perhaps one additional image, in accordance with embodiments.

Figure 1:
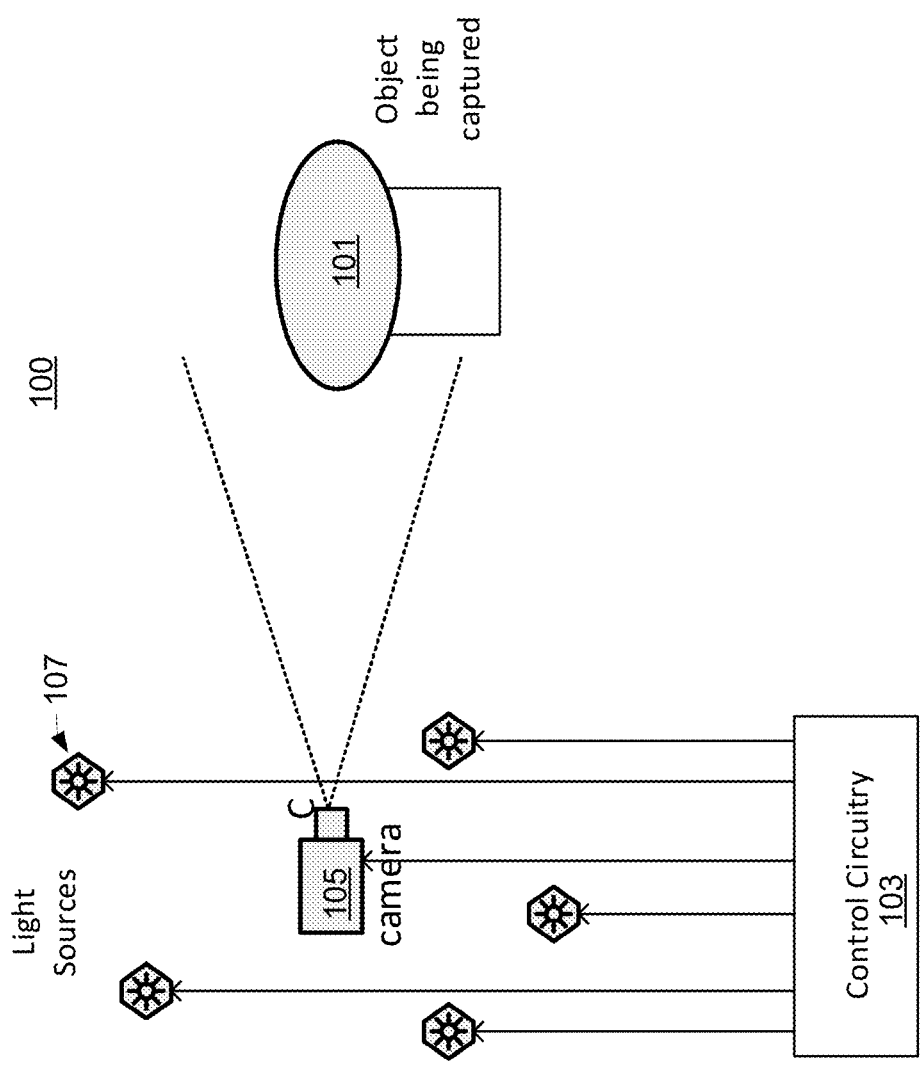
FIG. 1 shows an example environment in which embodiments may be practiced.

FIG. 1 shows an example environment in which embodiments may be practiced. In general, the light sources 107 illuminate the object 101 while the camera 105 captures images that contain glints. Glints are the reflections off from the object 101 due to the light sources 107. In one embodiment, a glint is mapped to a light source 107 that is responsible for the glint. As one non-limiting example each of the five depicted five light sources 107 may cause a separate glint. Thus, the system may uniquely map each of the glints to its respective light source 107.

The light sources 107 are light emitting diodes (LEDs), in one embodiment. The light sources 107 emit infrared (IR) light, in one embodiment. The light sources 107 can be positioned in a manner such that the majority (or all) of the light sources 107 will reflect glints to the camera 105. The light sources 107 are substantially fixed in position relative to the object 101, in one embodiment. Note that the object 101 could move somewhat, such as in the movement of a person's eye. In some embodiments, the light sources 107, the object 101 and the camera 105 are fixed (or at least substantially fixed) in absolute position. In some embodiments, the relative position of the light sources 107 to the object 101 and/or camera 105 is fixed (or at least substantially fixed). However, the absolute positions may change substantially. For example, a person could be walking while wearing an apparatus that contains the light sources 107, as well as the camera 105.

The control circuitry 103 is configured to control the light sources 107. In one embodiment, the light sources 107 are turned on or off to create certain patterns of illumination. Separate images are captured by the camera 105 for each of the patterns. The control circuitry 103 is able to synchronize the operation of the camera 105 to the patterns of illumination in order to capture an image for each pattern. The control circuitry 103 is able to control the exposure for each image. This can be useful if the different patterns result in different illumination levels. For example, one pattern may have all of the light sources 107 on, while another may have one or more light sources 107 off.

The control circuitry 103 (or other logic) analyzes the images to map glints to light sources 107. The control circuitry 103 may be any combination of software and/or hardware. For example, all, or a portion, of the logic implemented by the control circuitry 103 could be implemented by executing processor executable instructions on a processor.

As noted, the object 101 may be stationary relative to the camera 105 or moving somewhat relative to the camera 105. The camera 105 may be a high speed camera, such that motion between captured images is kept small. In one embodiment, one image is captured with all of the light sources 107 on ("All On image"). The control circuitry 103 is able to spatially synchronize features in the different images (such as glints) using this All On image. In other words, a glint may appear in a slightly different pixel location in different images due to slight motions between the object 101 and the camera 105 and/or the light source 107 responsible for the glint. The control circuitry 103 is to make corrections such that the glint is in a uniform pixel location for all images.

In one embodiment, the object 101 is an eye (e.g., a human eye). In such an embodiment, the glints can be used to generate a reconstruction of eye geometry, such as the cornea sphere. Eye gaze can be determined based on the eye geometry. This may also be referred to as determining a 3D eye vector. However, note that many other applications are possible for the glints, such as object recognition, high speed motion tracking, and production line control. Thus, the object 101 need not be an eye.

Figure 2:
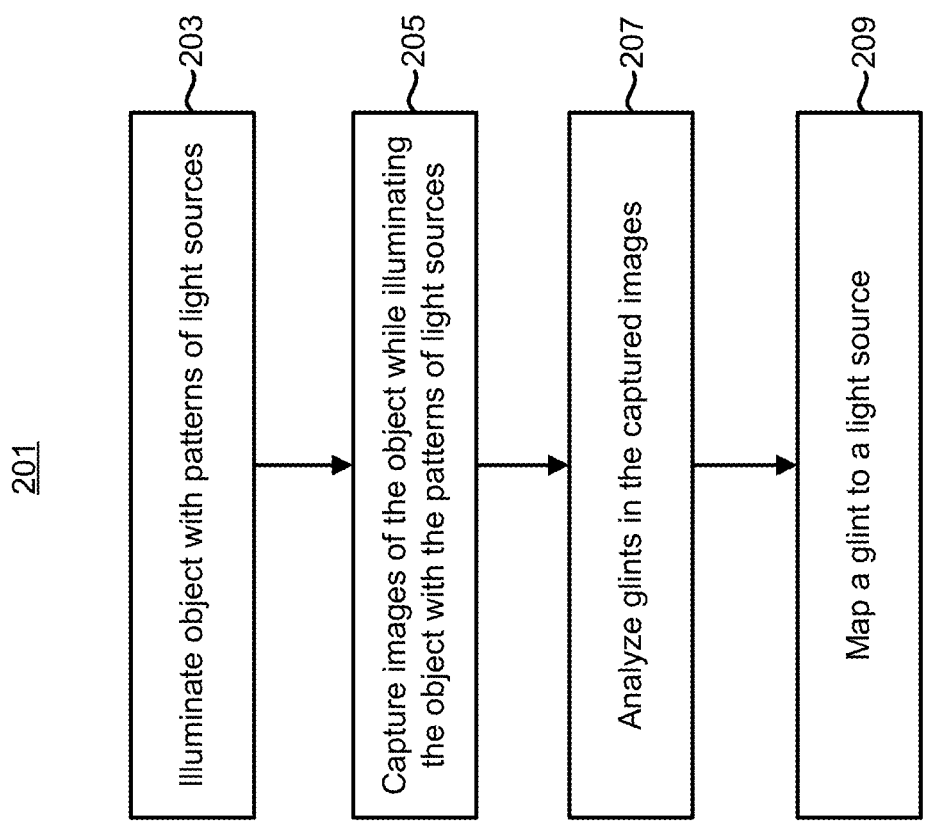
FIG. 2 is a flowchart of one embodiment of a process of mapping a glint to a light source.

FIG. 2 is a flowchart of one embodiment of a process 201 of mapping a glint to a light source 107. Reference will be made to the system of FIG. 1; however, it will be understood that the process 201 is not limited to the system of FIG. 1.

In step 203, an object 101 is illuminated with light sources 107. For example, control circuitry 103 controls the light sources 107 to illuminate the object 101 with certain patterns. A pattern is defined by which light source(s) is on and which light source(s) (if any) are off. For example, one pattern has all light sources 107 on. Another pattern has exactly one of the light sources 107 off and all of the remaining light sources 107 on. There could be such a "one on" pattern for each of the light sources 107. Still another pattern may have two or more of the light sources 107 on, with the rest off.

Figure 6A:
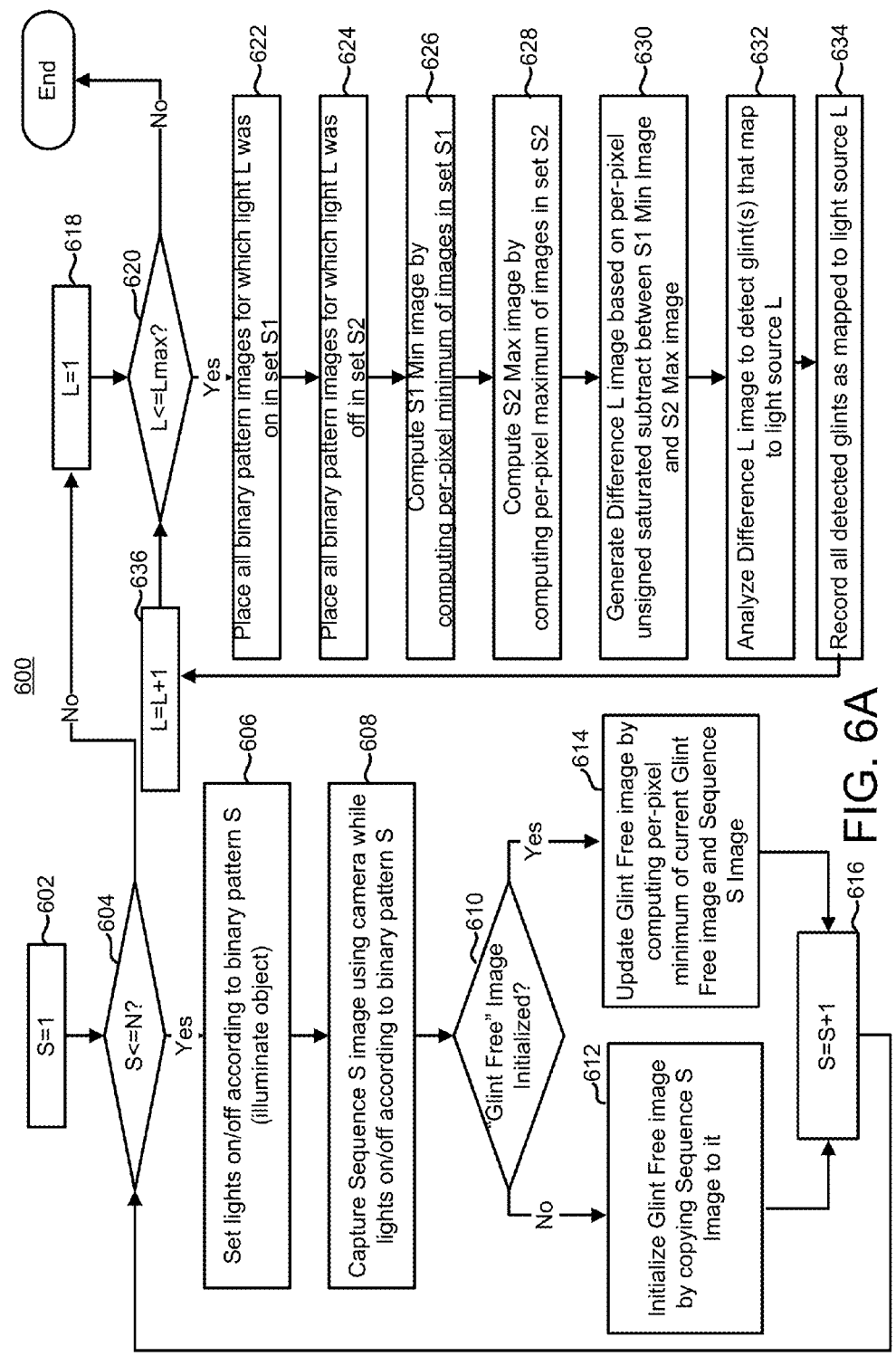
FIG. 6A is a flowchart of one embodiment of a process in which glints can be mapped to up to $2^N-2$ light sources while capturing N images that correspond to N different patterns.

In some embodiments, the patterns include a first pattern in which a first light source 107 is on and a second pattern in which the first light source 107 is off. As one example, in the first pattern all of the light sources 107 are on. However, in the second pattern only the first light source 107 is off—with the rest of the light sources 107 on. FIG. 5 describes one embodiment of this technique. However, note that this is just one example. Another example is for the first pattern to have the first light source 107 on and one or more of the other light sources 107 off. Then, in the second pattern, the first light source 107 and zero or more of the other light sources 107 are off. FIG. 6A describes one embodiment of this technique.

In some embodiments, each of the light sources 107 is off for at least one of the patterns and on for at least one of the patterns. This could include exactly one light source 107 being off for a given pattern, with such a pattern for each light source. FIG. 5 describes one embodiment of this technique. This could also include two or more light sources being off for a given pattern. FIG. 6A describes one embodiment of this technique.

In step 205, the control circuitry 103 causes the camera 105 to capture images while illuminating the object 101 with corresponding ones of the patterns. That is, one image may be captured for each pattern. In one embodiment, the camera 105 is a high speed camera 105 such that the images can be captured over a very short time period. It can be desirable for the images to be captured over a period of time in which the object 101 does not move a great deal. Some amount of movement can be dealt with.

In step 207, glints in the images are analyzed. This could be performed by the control circuitry 103, or other logic. The analysis may involve performing a set of operations on certain ones of the images that are designed to detect glints for a specific one of the light sources 107. That is, whatever glint or glints that are detected as a result of the operations are known to map to the specific light source 107. The specific images that are selected for processing may depend on which light source 107 is being processed. Also, the specific operations that are performed on the images may depend on what patterns are used to illuminate the object 101, as well as which light source 107 is being processed.

In one embodiment, step 207 includes comparing differences between one image and another image. As one example, an image that was captured with exactly one light source 107 off may be compared with an image captured when all light sources 107 are on to look for a glint that is missing in the image that was captured with exactly one light source 107 off. In one embodiment, step 207 includes computing a per-pixel difference image between the All On image and an image with just one light source 107 off. Further details are discussed below in connection with the discussion of FIG. 5.

In one embodiment, step 207 includes performing a per-pixel minimum of one or more images to produce a "min image." This can be for a set of images in which a first light source 107 is on. In one embodiment, step 207 includes performing a per-pixel maximum of one or more images to produce a "max image." This can be for a set of images in which the first light source 107 is off. In one embodiment, step 207 includes computing a per-pixel difference image that is the per-pixel unsigned saturated subtract operation of the max image subtracted from the min image. Further details are discussed below in connection with the discussion of FIG. 6A.

In step 209, a glint is mapped to a light source 107 based on the analysis of step 207. In some embodiments, the analysis of step 207 produces an image that contains whatever glints map to the light source 107 currently being analyzed. Although step 209 is phrased as mapping a glint to a light source, it will be understood that glints can be mapped to all of the light sources 107 by suitable analysis in step 207.

Prior to discussing further details, an example device and application will be discussed. An example application is gaze detection. Gaze is sometimes referred to as a line of sight from the user's eye to an object, real or virtual, at which the user is looking. Embodiments are not limited to either this example device or this example application.

Figure 3A:
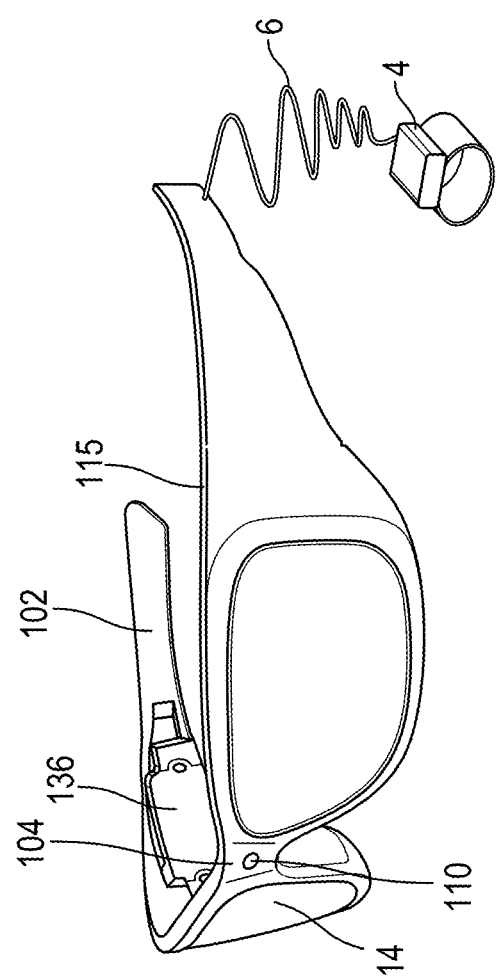
FIG. 3A is a block diagram depicting example components of an embodiment of a mixed reality display system.

FIG. 3A is a block diagram depicting example components of one embodiment of a mixed reality display system with gaze determination. System 10 includes a see-through display device as a near-eye, head mounted display device 2 in communication with processing unit 4 via wire 6. In other embodiments, head mounted display device 2 communicates with processing unit 4 via wireless communication. Processing unit 4 may take various embodiments. In some embodiments, processing unit 4 is a separate unit which may be worn on the user's body, e.g. the wrist in the illustrated example or in a pocket, and includes much of the computing power used to operate near-eye display device 2. Processing unit 4 may communicate wirelessly (e.g., WiFi, Bluetooth, infra-red, or other wireless communication means) to one or more computing systems (not depicted in FIG. 3A). In other embodiments, the functionality of the processing unit 4 may be integrated in software and hardware components of the display device 2.

Head mounted display device 2, which in one embodiment is in the shape of eyeglasses in a frame 115, is worn on the head of a user so that the user can see through a display, embodied in this example as a display optical system 14 for each eye, and thereby have an actual direct view of the space in front of the user. Frame 115 provides a support for holding elements of the system in place as well as a conduit for electrical connections. In this embodiment, frame 115 provides a convenient eyeglass frame as support for the elements of the system discussed further below. In other embodiments, other support structures can be used. An example of such a structure is a visor or goggles. The frame 115 includes a temple or side arm for resting on each of a user's ears. Temple 102 is representative of an embodiment of the right temple. Nose bridge 104 of the frame includes a microphone 110 for recording sounds and transmitting audio data to processing unit 4. In one embodiment, the processing unit 4 unit is part of a mobile device, such as a smart cellular telephone. Some other examples of mobile devices 5 are a laptop or notebook computer and a netbook computer. Processing unit 4 could also be a desktop or other computing system.

Figure 3B:
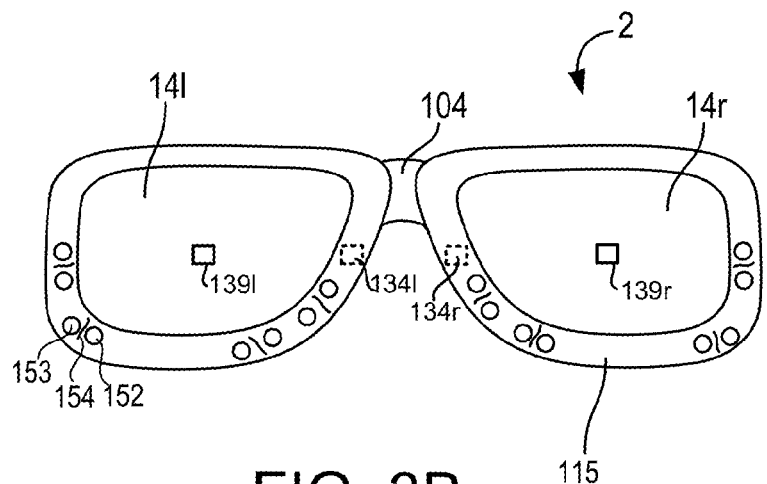
FIG. 3B illustrates an exemplary arrangement of positions of respective sets of gaze detection elements in a gaze detection system for each eye positioned facing each respective eye on a mixed reality display device embodied in a set of eyeglasses.

FIG. 3B illustrates an exemplary arrangement of positions of respective sets of gaze detection elements in a gaze detection system for each eye positioned facing each respective eye by a see-through, near-eye, mixed reality display system embodied in a set of eyeglasses 2. What appears as a lens for each eye represents a display optical system 14 for each eye, e.g. 14r and 14l. A display optical system includes a see-through lens, as in an ordinary pair of glasses, but also contains optical elements (e.g. mirrors, filters) for seamlessly fusing virtual content with the actual and direct real world view seen through the lens. A display optical system 14 has an optical axis which is generally in the center of the see-through lens in which light is generally collimated to provide a distortionless view. For example, when an eye care professional fits an ordinary pair of eyeglasses to a user's face, a goal is that the glasses sit on the user's nose at a position where each pupil is aligned with the center or optical axis of the respective lens resulting in generally collimated light reaching the user's eye for a clear or distortionless view.

In the example of FIG. 3B, a detection area 139r, 139l of at least one sensor is aligned with the optical axis of its respective display optical system 14r, 14l so that the center of the detection area 139r, 139l is capturing light along the optical axis. If the display optical system 14 is aligned with the user's pupil, each detection area 139 of the respective sensor 134 is aligned with the user's pupil. Reflected light of the detection area 139 is transferred via one or more optical elements to the actual image sensor 134 of the camera, in this example illustrated by dashed line as being inside the frame 115.

In one example, a visible light camera also commonly referred to as an RGB camera may be the sensor, and an example of an optical element or light directing element is a visible light reflecting mirror which is partially transmissive and partially reflective. The visible light camera provides image data of the pupil of the user's eye, while IR photodetectors 152 capture glints which are reflections in the IR portion of the spectrum. If a visible light camera is used, reflections of virtual images may appear in the eye data captured by the camera. An image filtering technique may be used to remove the virtual image reflections if desired. An IR camera is not sensitive to the virtual image reflections on the eye. The IR photodetectors 152 may be used for one implementation of the camera 105 that captures glints from the object 101. However, other sensors could be used in addition to or instead of the IR photodetectors 152 to capture glints.

In other examples, the at least one sensor 134 is an IR camera or a position sensitive detector (PSD) to which IR radiation may be directed. For example, a hot reflecting surface may transmit visible light but reflect IR radiation. The IR radiation reflected from the eye may be from incident radiation of the illuminators 153, other IR illuminators (not shown) or from ambient IR radiation reflected off the eye. The illuminators 153 are one embodiment of the light sources 107 that are used to illuminate the object 101.

In some examples, sensor 134 may be a combination of an RGB and an IR camera, and the optical light directing elements may include a visible light reflecting or diverting element and an IR radiation reflecting or diverting element. In some examples, a camera may be small, e.g. 2 millimeters (mm) by 2 mm. An example of such a camera sensor is the Omnivision OV7727. In other examples, the camera may be small enough, e.g. the Omnivision OV7727, e.g. that the image sensor or camera 134 may be centered on the optical axis or other location of the display optical system 14. For example, the camera 134 may be embedded within a lens of the system 14. Additionally, an image filtering technique may be applied to blend the camera into a user field of view to lessen any distraction to the user.

In the example of FIG. 3B, there are four sets of an illuminator 153 paired with a photodetector 152 and separated by a barrier 154 to avoid interference between the incident light generated by the illuminator 153 and the reflected light received at the photodetector 152. To avoid unnecessary clutter in the drawings, drawing numerals are shown with respect to a representative pair. Each illuminator may be an infra-red (IR) illuminator which generates a narrow beam of light at about a predetermined wavelength. Each of the photodetectors may be selected to capture light at about the predetermined wavelength. Infra-red may also include near-infrared. As there can be wavelength drift of an illuminator or photodetector or a small range about a wavelength may be acceptable, the illuminator and photodetector may have a tolerance range about a wavelength for generation and detection. In embodiments where the sensor is an IR camera or IR position sensitive detector (PSD), the photodetectors may be additional data capture devices and may also be used to monitor the operation of the illuminators, e.g. wavelength drift, beam width changes, etc. The photodetectors may also provide glint data with a visible light camera as the sensor 134.

Figure 3C:
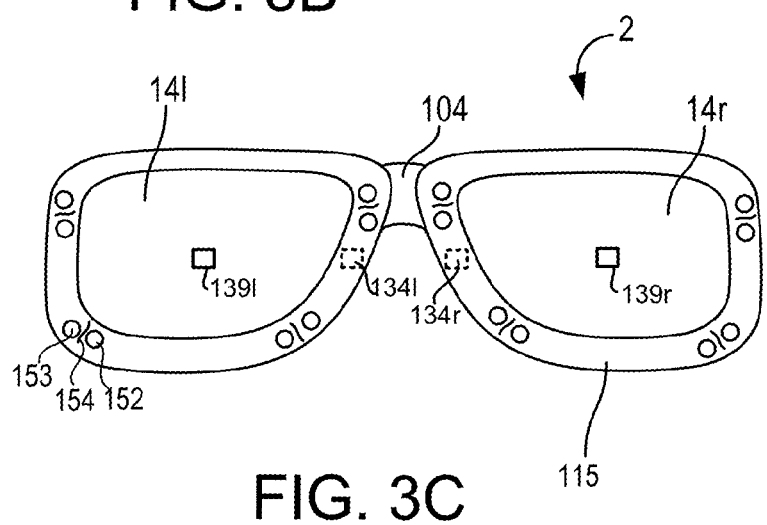
FIG. 3C illustrates another exemplary arrangement of positions of respective sets of gaze detection elements in a gaze detection system for each eye positioned facing each respective eye on a mixed reality display device embodied in a set of eyeglasses.

FIG. 3C illustrates another exemplary arrangement of positions of respective sets of gaze detection elements in a gaze detection system for each eye positioned facing each respective eye on a mixed reality display device embodied in a set of eyeglasses. In this embodiment, two sets of illuminator 153 and photodetector 152 pairs are positioned near the top of each frame portion 115 surrounding a display optical system 14, and another two sets of illuminator and photodetector pairs are positioned near the bottom of each frame portion 115 for illustrating another example of a geometrical relationship between illuminators and hence the glints they generate. This arrangement of glints may provide more information on a pupil position in the vertical direction.

Figure 3D:
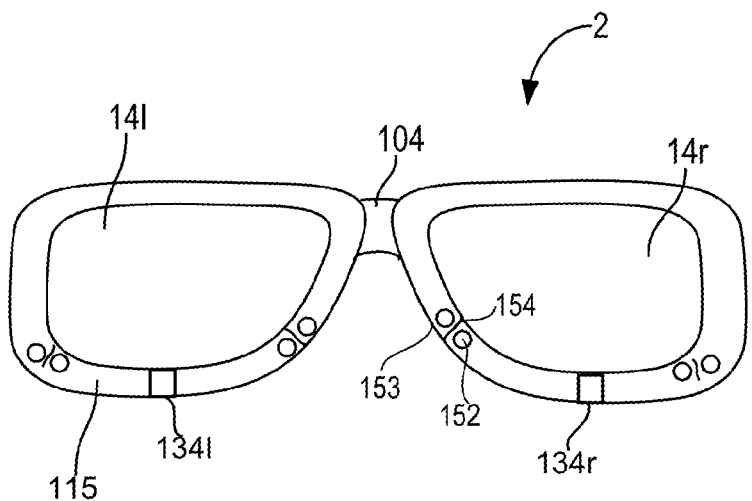
FIG. 3D illustrates yet another exemplary arrangement of positions of respective sets of gaze detection elements in a gaze detection system for each eye positioned facing each respective eye by the set of eyeglasses.

FIG. 3D illustrates yet another example arrangement of positions of respective sets of gaze detection elements in a gaze detection system for each eye positioned facing each respective eye by the set of eyeglasses. In this example, the sensor 134r, 134l is in line or aligned with the optical axis of its respective display optical system 14r, 14l but located on the frame 115 below the system 14. Additionally, in some embodiments, the camera 134 may be a depth camera or include a depth sensor. In this example, there are two sets of illuminators 153 and photodetectors 152.

Figure 4A:
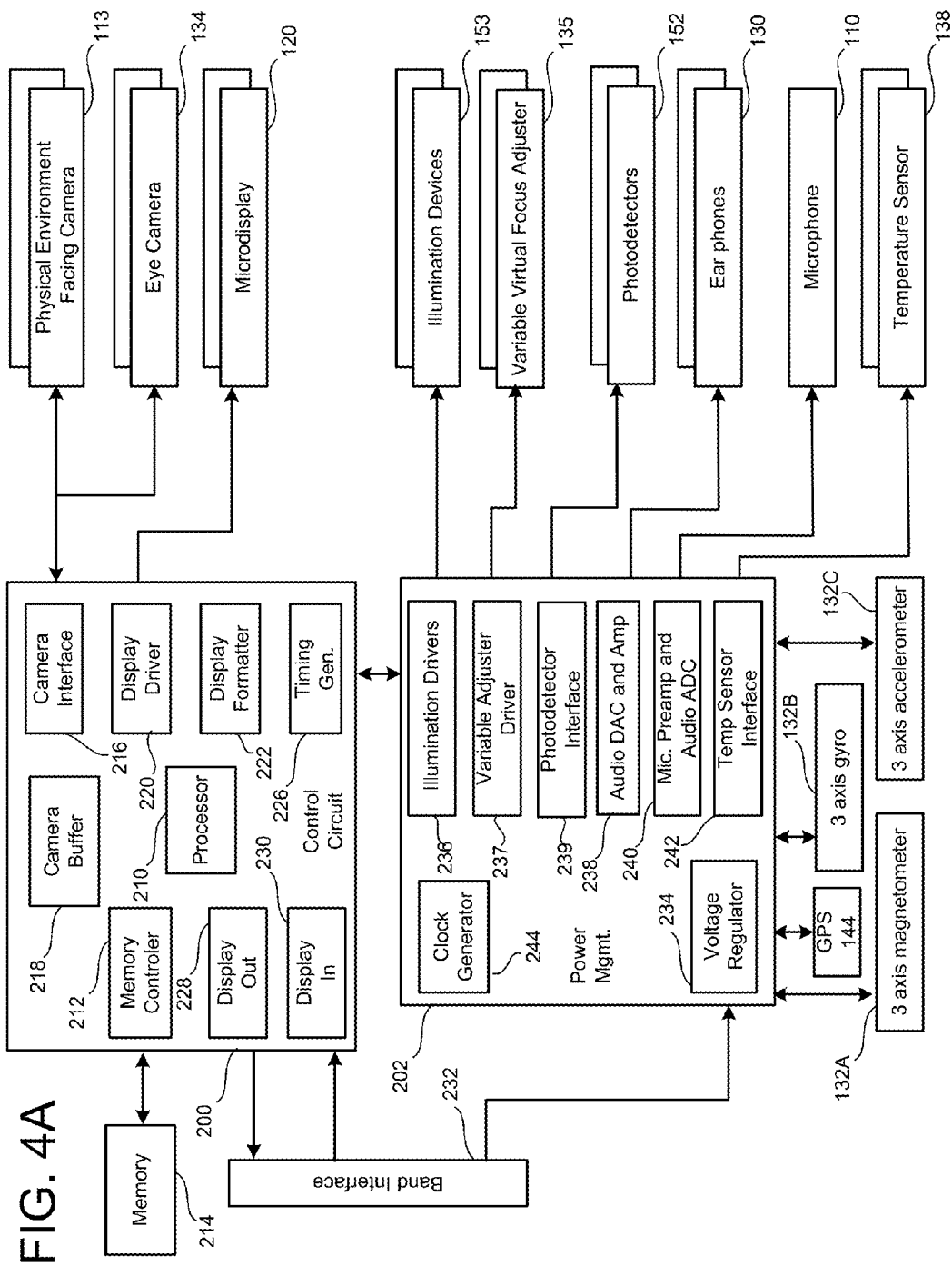
FIG. 4A is a block diagram of one embodiment of hardware and software components of a see-through, near-eye, mixed reality display unit as may be used with the embodiments described in this disclosure.
Figure 4B:
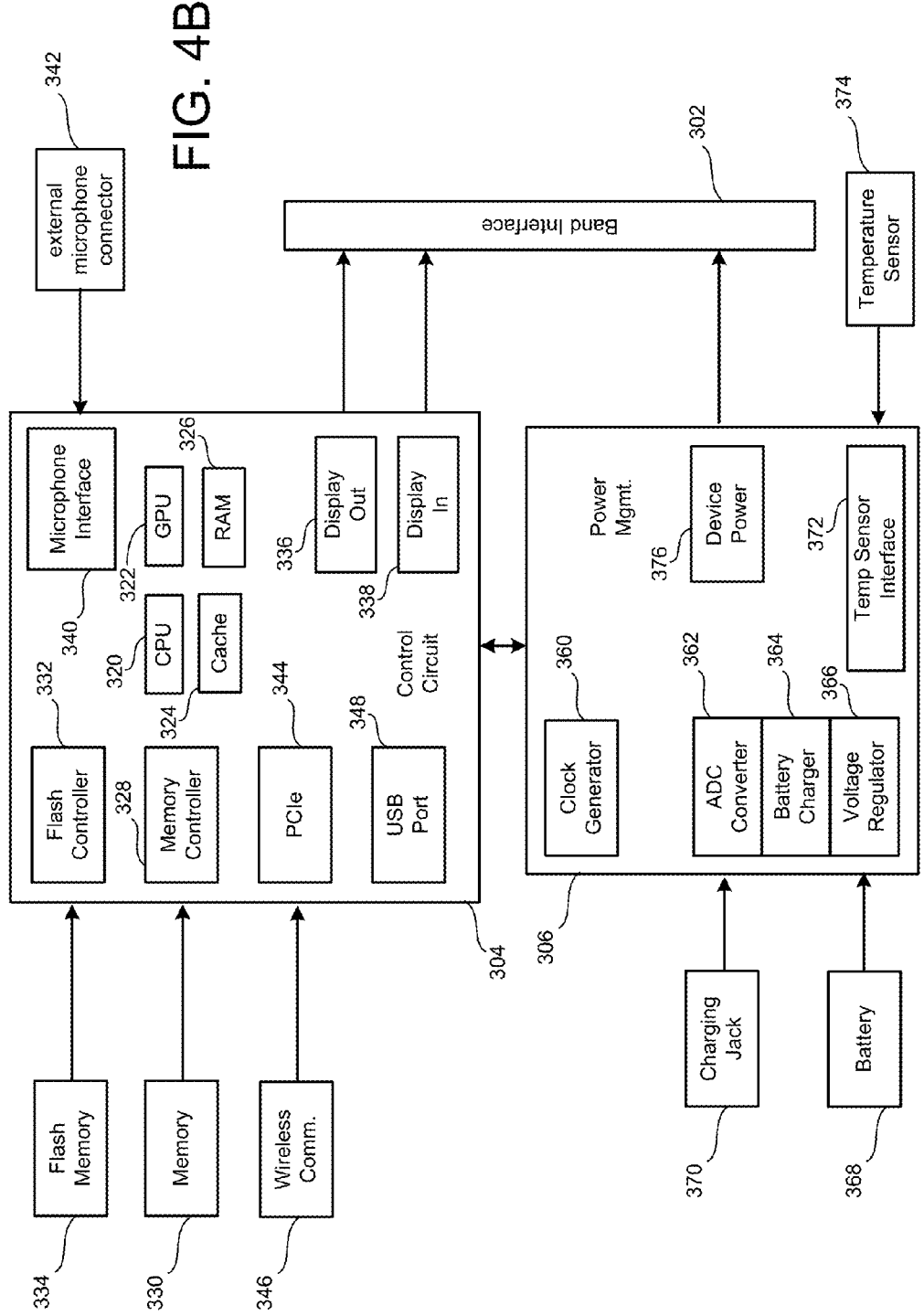
FIG. 4B is a block diagram of one embodiment of the hardware and software components of a processing unit associated with a see-through, near-eye display unit.

FIG. 4A is a block diagram of one embodiment of hardware and software components of a see-through, near-eye, mixed reality display unit as may be used with the embodiments described in this disclosure. FIG. 4B is a block diagram describing the various components of processing unit 4. In this embodiment, near-eye display device 2, receive instructions about a virtual image from processing unit 4 and provides the sensor information back to processing unit 4. Processing unit 4, the components of which are depicted in FIG. 4B, will receive the sensory information from the display device 2. Based on that information, processing unit 4 will determine where and when to provide a virtual image to the user and send instructions accordingly to the control circuitry 136 of the display device 2.

Note that some of the components of FIG. 4A (e.g., physical environment facing camera 113, eye camera 134, variable virtual focus adjuster 135, photodetector interface 139, micro display 120, illumination device 153 or illuminators, earphones 130, and temperature sensor 138) are shown in shadow to indicate that there are two of each of those devices, one for the left side and one for the right side of head mounted display device 2. FIG. 4A shows the control circuit 200 in communication with the power management circuit 202. Control circuit 200 includes processor 210, memory controller 212 in communication with memory 214 (e.g., D-RAM), camera interface 216, camera buffer 218, display driver 220, display formatter 222, timing generator 226, display out interface 228, and display in interface 230. In one embodiment, all of components of control circuit 220 are in communication with each other via dedicated lines of one or more buses. In another embodiment, each of the components of control circuit 200 are in communication with processor 210.

Camera interface 216 provides an interface to the two physical environment facing cameras 113 and each eye camera 134 and stores respective images received from the cameras 113, 134 in camera buffer 218. Display driver 220 will drive microdisplay 120. Display formatter 222 may provide information, about the virtual image being displayed on microdisplay 120 to one or more processors of one or more computer systems, e.g. 4, 12, 210 performing processing for the augmented reality system. Timing generator 226 is used to provide timing data for the system. Display out 228 is a buffer for providing images from physical environment facing cameras 113 and the eye cameras 134 to the processing unit 4. Display in 230 is a buffer for receiving images such as a virtual image to be displayed on microdisplay 120. Display out 228 and display in 230 communicate with band interface 232 which is an interface to processing unit 4.

Power management circuit 202 includes voltage regulator 234, eye tracking illumination driver 236, variable adjuster driver 237, photodetector interface 239, audio DAC and amplifier 238, microphone preamplifier and audio ADC 240, temperature sensor interface 242 and clock generator 244. Voltage regulator 234 receives power from processing unit 4 via band interface 232 and provides that power to the other components of head mounted display device 2. Illumination driver 236 controls, for example via a drive current or voltage, the illumination devices 153 to operate about a predetermined wavelength or within a wavelength range. Audio DAC and amplifier 238 receives the audio information from earphones 130. Microphone preamplifier and audio ADC 240 provides an interface for microphone 110. Temperature sensor interface 242 is an interface for temperature sensor 138. Power management unit 202 also provides power and receives data back from three axis magnetometer 132A, three axis gyro 132B and three axis accelerometer 132C. Power management unit 202 also provides power and receives data back from and sends data to GPS transceiver 144.

The variable adjuster driver 237 provides a control signal, for example a drive current or a drive voltage, to the adjuster 135 to move one or more elements of the microdisplay assembly 173 to achieve a displacement for a focal region calculated by software executing in the a processor 210 of the control circuitry 13, or the processing unit 4,5 or the hub computer 12 or both. In embodiments of sweeping through a range of displacements and, hence, a range of focal regions, the variable adjuster driver 237 receives timing signals from the timing generator 226, or alternatively, the clock generator 244 to operate at a programmed rate or frequency.

The photodetector interface 239 performs any analog to digital conversion needed for voltage or current readings from each photodetector, stores the readings in a processor readable format in memory via the memory controller 212, and monitors the operation parameters of the photodetectors 152 such as temperature and wavelength accuracy.

FIG. 4B is a block diagram of one embodiment of the hardware and software components of a processing unit 4 associated with a see-through, near-eye display unit. FIG. 4B shows controls circuit 304 in communication with power management circuit 306. Control circuit 304 includes a central processing unit (CPU) 320, graphics processing unit (GPU) 322, cache 324, RAM 326, memory control 328 in communication with memory 330 (e.g., D-RAM), flash memory controller 332 in communication with flash memory 334 (or other type of non-volatile storage), display out buffer 336 in communication with see-through, near-eye display device 2 via band interface 302 and band interface 232, display in buffer 338 in communication with near-eye display device 2 via band interface 302 and band interface 232, microphone interface 340 in communication with an external microphone connector 342 for connecting to a microphone, PCI express interface for connecting to a wireless communication device 346, and USB port(s) 348.

In one embodiment, wireless communication component 346 can include a Wi-Fi enabled communication device, Bluetooth communication device, infrared communication device, etc. The USB port can be used to dock the processing unit 4 to another computing device in order to load data or software onto processing unit 4 as well as charge processing unit 4. In one embodiment, CPU 320 and GPU 322 are the main workhorses for determining where, when and how to insert virtual images into the view of the user.

Power management circuit 306 includes clock generator 360, analog to digital converter 362, battery charger 364, voltage regulator 366, see-through, near-eye display power source 376, and temperature sensor interface 372 in communication with temperature sensor 374 (located on the wrist band of processing unit 4). An alternating current to direct current converter 362 is connected to a charging jack 370 for receiving an AC supply and creating a DC supply for the system. Voltage regulator 366 is in communication with battery 368 for supplying power to the system. Battery charger 364 is used to charge battery 368 (via voltage regulator 366) upon receiving power from charging jack 370. Device power interface 376 provides power to the display device 2.

FIG. 5 is a flowchart of one embodiment of a process 500 of mapping glints to light sources 107 that involves turning off one light source 107 at a time. The process 500 is one embodiment of the process 201 of FIG. 2. This process 500 also describes how a glint free image may be generated. In step 502, all light sources 107 are turned on by, for example, control circuitry 103.

In step 504, the camera 105 captures an image while all of the light sources 107 are illuminating the object 101. This, "All On" image may be used to help refine and spatially synchronize the results. For example, the object 101 and/or the camera 105 and/or the light sources 107 could be moving, wherein there could be slight differences in the locations of the glints in the captured images.

In step 506, the image that was captured with all light sources 107 on is copied to a working glint free image. Since all the light sources 107 are on at this time, there will be glints in the working glint free image. During process 500, the working glint free image gets updated to remove glints from it until it becomes free of glints.

In step 508, a counter ("L") for the light source 107 being processed is initialized to "1". Control then passes to step 512. Steps 512-522 pertain to processing one of the light sources 107, which will be referred to as light source "L". That is, steps 512-522 may be performed once for each light source 107. In step 512, all light sources 107 but light source L are turned on. Stated another way, a pattern is created having light source L off and the rest of the light sources on. In step 514, an image is captured by the camera 105 while the object 101 is being illuminated as described in step 512. This image will be referred to as "Glint L" image.

In step 516, the working glint free image is updated by computing a per-pixel minimum of the current working glint free image and the glint L image. This has the effect of removing the glint that is associated with the light source L, which is off.

In step 518, a "Difference L Image" is generated based on per-pixel differences between the image with all light on and the current glint L image. In one embodiment, an unsigned saturated subtract operation is performed. In such an operation, the glint L image may be subtracted from the All On image. This may be expressed as follows: Diff(A,B), where A is the All On image and B is the Glint L Image. Alternatively, this may be expressed as Max(0, A−B). Thus, with such an operation, if the result of a given pixel in image B being subtracted from the corresponding pixel in image A results in a value below zero (underflow), the value is set to 0 for that pixel. As noted, these operations are performed on a per-pixel basis.

In step 520, the Difference L Image is analyzed to detect glint(s) that map to light source L. Note that it is possible for there to be more than one glint per light source 107. One way this could happen is if the object is a person's eye and the person is wearing eyeglasses. Another possibility is for the light from a given light source 107 to reflect off from both the cornea and the sclera and back to the camera 105, thus resulting in two glints. Steps 518-520 may in effect compare the image with light source L off to the All On image to determine which glint is missing in the image with light source L off.

In step 522, all detected glints in the Difference L Image are recorded as mapping to light source L. Step 524 increments the counter of light sources. Control then passes to step 510. In step 510, the control logic 103 determines whether there are more light sources 107 to process. If so, control passes to step 512 to process the next light source 107. If not, then the process 500 then goes to step 526 in which the working glint free image is marked as a final glint free image. The process 500 then ends. Note that when the process 500 ends, all of the light sources 107 will have been turned off once (with all other light sources 107 on).

As previously noted, the All On image can be used for refinement of results, as well as spatial synchronization of features in images. Note that in process 500, after each light source L has been processed, refinement/synchronization against the All On image can be performed immediately. An example of how glints can be spatially synchronized is by taking the glint locations as detected in the various images, and running a local peak analysis algorithm around that location in the "All On" image to refine to location of that glint if it has moved. A similar approach can be taken in refining results of the "Glint-Free" image analysis. Since "Glint-Free" image is a combination of multiple images, motion can introduce significant error to unsynchronized results.

The process 500 of FIG. 5 described one embodiment in which n+1 images were used to map glints to "n" light sources 107. That is, there was an "All On" pattern and a pattern for each light source 107 in which it was the only light source 107 that was off.

It is not required that there be at least one image per light source 107 in order to map glints to light sources 107. Fewer images can be used. In one embodiment, N images can be used to map glints to $2^N-2$ light sources. For example, three images can be used to map glints to up to six light sources 107. As another example, four images can be used to map glints to up to 14 light sources. As another example, two images can be used to map glints to two light sources.

FIG. 6A is a flowchart of one embodiment of a process 600 in which glints can be mapped to up to $2^N-2$ light sources 107 while capturing N images that correspond to N different patterns. The process 600 also describes how a glint free image can be generated. Process 600 is one embodiment of process 201.

In step 602, a pattern counter ("S") is initialized to "1". This pattern counter is for the N different patterns of light sources that will be used to illuminate the object 101. In step 604, a determination is made whether all of the patterns have been used to illuminate the object 101. That is, the pattern counter "S" is compared to the number of patterns "N." Control passes to step 606, assuming that all patterns have not yet been used.

In step 606, the control circuitry 103 sets the light sources 107 on or off according to the present pattern. For the sake of discussion, this will be referred to as "binary pattern S." There will be a total of N binary patterns, in one embodiment.

In step 608, an image is captured by the camera 105 while the present pattern is illuminating the object 101. For the sake of discussion, this will be referred to as "Sequence S." Prior to further discussion of FIG. 6A, some examples of binary patterns will be discussed.

As one simple example, the total number of light sources 107 may be two. In this case, two binary patterns may be used to map glints to the two light sources 107. Thus, two images are captured in this example.

Table I shows how glints can be mapped to two light sources 107 using two binary patterns. In pattern A, light source L1 is off and light source L2 is on. In pattern B, light source L1 is on and light source L2 is off. The "All On" pattern is not required to map the glints to the two light sources, but is shown as one possible additional pattern.

TABLE I

| Light Source | Pattern A | Pattern B | All On |
| --- | --- | --- | --- |
| L1 | Off | On | On |
| L2 | On | Off | On |

As a slightly more complex example, the total number of light sources may be six. In this case, three binary patterns may be used to map glints to the six light sources 107. Thus, three images may be captured in this example. Table II shows how three images may be captured to map glints to six light sources (L1-L6). In this table, a "0" means that the light is off and a "1" means that the light is on for that pattern.

TABLE II

| Light Source | Pattern A | Pattern B | Pattern C | All On |
| --- | --- | --- | --- | --- |
| L1 | 0 | 0 | 1 | 1 |
| L2 | 0 | 1 | 0 | 1 |
| L3 | 0 | 1 | 1 | 1 |
| L4 | 1 | 0 | 0 | 1 |

TABLE II-continued

| Light Source | Pattern A | Pattern B | Pattern C | All On |
| --- | --- | --- | --- | --- |
| L5 | 1 | 0 | 1 | 1 |
| L6 | 1 | 1 | 0 | 1 |
| L7* | 1 | 1 | 1 | 0 |
| L8* | 1 | 1 | 1 | 0 |
| L9* | 1 | 1 | 1 | 0 |

Light sources L7-L9 are not required. These are light sources that are used for additional illumination. However, these are "non-detectable" light sources, in this example. A non-detectable light source is one for which glints are not mapped. One consequence of using light sources L7-L9, as described in the table, is that there will always be six light sources on, which means that illumination intensity may be uniform.

One option in process 600 is to generate a glint free image. Steps 610-614 may optionally be performed to generate a glint free image. In step 610, it is determined whether a glint free image has yet been initialized. If not, then control passes to step 612 to initialize the glint free image by copying the Sequence S image to the glint free image.

On the other hand, if the glint free image has already been initialized, then control passes to step 614. In step 614, the glint free image is updated by computing a per-pixel minimum of the current glint free image and the Sequence S image.

In either event, the process 600 then continues on to step 616 to increment the counter of the binary patterns. Control then passes to step 604 to determine whether there are more binary patterns to be used to illuminate the object 101. When all binary patterns have been used, control passes to step 618. In steps 618-636, the captured images are processed to map the glints to the light sources 107. These steps may be performed separately for each of the light sources 107. Note that the steps can be performed in parallel, as the images have already been captured in steps 606-608.

In step 618, a counter of the number of light sources 107 is initialized to "1" to indicate that a glint is to be mapped to a first light source of the light sources 107. Step 620 is a test to determine whether all light sources 107 have been processed. If not, control passes to step 622. Briefly, steps 622 and 624 place each of the images that were captured in step 608 into one of two sets (S1 or S2). Set S1 is for all of the images for which the current light source was on. Set S2 is for all of the images for which the current light source was off. Thus, in step 622, all binary patterns images for which light source L was on are placed into set S1. In step 624, all binary patterns images for which light source L was off are placed into set S2.

The following will be used to illustrate. Referring back to Table II, an example of processing light source L1 will be discussed. Light source L1 is on for pattern C. Thus the image captured when pattern C was used to illuminate the object 101 will be placed into set S1. Light source L1 is off for patterns A and B. Thus, the images captured when patterns A and B were used to illuminate the object 101 will be placed into set S2. Similar reasoning applied to other light sources L2-L6 in Table II. Note that Table II is just one example of binary patterns, others could be used.

Continuing on with the flow, an "S1 Min Image" is computed by computing a per-pixel minimum of all of the images in set S1, in step 626. In the example from Table II for light source L1, there is only one image in set S1 (that being the C image). Thus, the per-pixel minimum of all of the images in set S1 will be that image. However, note that for light source L3, there are two patterns for which L3 is on. Thus, for light L3, the images captured when patterns B and C were used will be placed into set S1. Step 622 thus performs a per-pixel minimum between the two images captured when pattern B and pattern C were used to illuminate the object 107, for this example.

In step 626, an "S2 Max Image" is computed by computing a per-pixel maximum of all of the images in set S2. Referring again to the example of light source L1 in Table II, the images captured when patterns A and B were used to illuminate the object 101 were placed into set S2. Thus, step 626 performs a per-pixel maximum between the images captured when patterns A and B were used to illuminate the object 101, for this example. For some light sources 107, such as light source L3, there may by only one image in set S2.

Table III shows an example of how glints may appear in the various images for the example in which three binary patterns are used to map glints to six light sources L1-L6. A "1" indicates a bright pixel at the glint location. A "0" indicates a normal pixel at the glint location. In other words, a "1" indicates that the light source 107 which is responsible for the glint is on, and a "0" indicates that the light source 107 which is responsible for the glint is off

TABLE III

| Image | G1 | G2 | G3 | G4 | G5 | G6 | G7-G9* |
|---|---|---|---|---|---|---|---|
| A | 0 | 0 | 0 | 1 | 1 | 1 | 1 |
| B | 0 | 1 | 1 | 0 | 0 | 1 | 1 |
| C | 1 | 0 | 1 | 0 | 1 | 0 | 1 |
| All On | 1 | 1 | 1 | 1 | 1 | 1 | 0 |

In Table III, G7-G9 refer to glints due to optional lights L7-L9. Recall that these lights are on when capturing Images A-C for the purpose of creating additional illumination. However, glints G7-G9 are not detected in accordance with embodiments.

Table IV shows an example of how glints may appear in the various Min and Max images for the example in which three binary patterns are used to map glints to six light sources L1-L6. Table IV can be derived by applying the appropriate operation on the values of Table III. For example, the Min(A, B) only has a bright pixel where both the A Image and the B Image were bright. In other words, where either Image A or B had a normal pixel, the Min(A,B) Image is normal. As noted, glints G7-G9 are not detected in accordance with embodiments.

TABLE IV

| Min/Max | G1 | G2 | G3 | G4 | G5 | G6 | G7-G9* |
|---|---|---|---|---|---|---|---|
| Min(A, B) | 0 | 0 | 0 | 0 | 0 | 1 | 1 |
| Max(A, B) | 0 | 1 | 1 | 1 | 1 | 1 | 1 |
| Min(A, C) | 0 | 0 | 0 | 0 | 1 | 0 | 1 |
| Max(A, C) | 1 | 0 | 1 | 1 | 1 | 1 | 1 |
| Min(B, C) | 0 | 0 | 1 | 0 | 0 | 0 | 1 |
| Max(B, C) | 1 | 1 | 1 | 0 | 1 | 1 | 1 |
| Min(A, B, C, All) | 0 | 0 | 0 | 0 | 0 | 0 | 0 |

Continuing on with the process flow, a per-pixel difference image "Diff L" is computed in step 630. The per-pixel difference image may be computed based on a per-pixel unsaturated subtract between the S1 Min Image and the S2 Max Image. Specifically, the S2 Max Image is subtracted from the S1 Min Image, in one embodiment.

This operation may be expressed as follows: Diff(A,B), where A is the S1 Min Image and B is the S2 Max Image. Alternatively, this may be expressed as Max(0, A−B). Thus, with such an operation, if the result of a given pixel in image B being subtracted from a corresponding pixel in image A results in a value below zero (underflow), the value is set to 0 for that pixel. As noted, these operations are performed on a per-pixel basis.

In step 632, the Diff L image is analyzed to detect glint(s) that map to light source L. The pixels in Diff L that correspond to glints that map to light source L will have a much larger value (e.g., be brighter) than the rest of the Diff L image, in one embodiment. In other words, the other pixels will generally have values around zero, in one embodiment.

Table V shows an example of how calculating the per-pixel difference image allows the glints to be mapped to light sources for the example in which three binary patterns are used to map glints to six light sources L1-L6. In Table V, a "1" corresponds to a bright pixel and a dash ("-") to a near black pixel at the glint location. For example, Table V shows that glint G1 (corresponding to light source L1) should appear in the per-pixel Difference Image Diff(C,Max(A,B)).

TABLE V

| Diff | G1 | G2 | G3 | G4 | G5 | G6 | G7-G9 |
|---|---|---|---|---|---|---|---|
| Diff(Min(A, B), C) | — | — | — | — | — | 1 | — |
| Diff(C, Max(A, B)) | 1 | — | — | — | — | — | — |
| Diff(Min(A, C), B) | — | — | — | — | 1 | — | — |
| Diff(B, Max(A, C)) | — | 1 | — | — | — | — | — |
| Diff(Min(B, C), A) | — | — | 1 | — | — | — | — |
| Diff(A, Max(B, C)) | — | — | — | 1 | — | — | — |

Another way of viewing the information in Table V is that it shows how glint candidates may be found. For example, Glint 6 candidate: Diff(Min(A,B),C), etc. To further illustrate, glint candidates may be located for the example from Table I as follows. Recall that Table I shows how glints can be mapped to two light sources using two binary patterns. Glint 1 candidate is Diff(B,A). Glint 2 candidate is Diff(A,B).

In step 634, the glint (or glints) that was detected in the Diff L image is recorded as being mapped to light source L. Control then passes to step 636 to increment the light source counter such that the next light source 107 may be processed by repeating step 620-634. Eventually all light sources 107 are processed (step 620=no). After processing all light sources 107, the process 600 ends.

Note that the process 600 of FIG. 6A may allow for fewer images to be captured than the process 500 of FIG. 5. This reduces the overall exposure to the object 101 (e.g., person) being exposed to the illumination. It also saves power by allowing the camera 105 to be off for longer periods of time, as well as not requiring the light sources 107 to be on as much.

The process 600 of FIG. 6A may also reduce the temporal distance between the first and last images. This can allow for increased illumination exposure, if desired. It may also be possible to reduce the speed at which the algorithm is run on the camera 107.

The following describes details of how the binary sequences can be derived for the example of Table II. That is, this is for an example in which three binary patterns (and corresponding images) are used to map glints to six light sources. The principles can be extended to other cases such as two binary patterns for two light sources and four binary patterns for 14 light sources.

Step 1 is to select the number of binary patterns to use. In this example, three binary patterns are used.

Step 2 is to list all numbers using that many binary digits. In this example, the numbers using three binary digits are listed: 000, 001, 010, 011, 100, 101, 110, 111.

Step 3 is to delete the first and last numbers. That is, the all "0" and the all "1" cases are not used.

Step 4 is to define the binary pattern of lights according to each significant digit of the remaining numbers. In this example, the binary patterns are: 000111, 011001, 101010. Note that this sequence of binary patterns is depicted in Table II. For purpose of discussion, this sequence of three binary patterns will be referred to as A, B, and C, in order.

Note that each glint in the sequence can be derived using AND and "AND NOT" operations. For a given image, a MIN operation can be used in lieu of AND. Likewise, a DIFF(a,b) operation can be used in lieu of "AND NOT."

Also note that A "AND NOT" B "AND NOT" C can also be written as A "AND NOT" (B OR C). On a given image a MAX operation can be used in lieu of an OR operation.

Figure 6B:
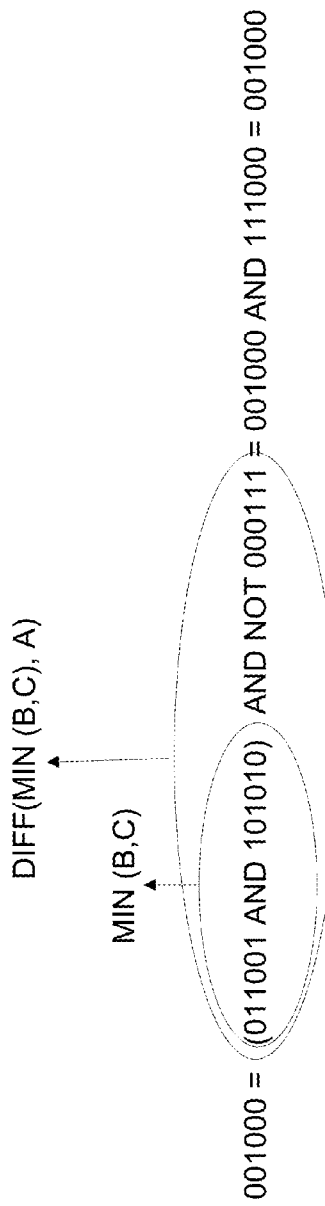
FIG. 6B and FIG. 6C shows examples for determining suitable operations performed during the process of FIG. 6A.

The examples FIGS. 6B and 6B will be used to further illustrate. FIG. 6B shows an example for "001000." The example shows a number of equivalent expressions, which are expressed in terms of operators "AND", as well as "AND NOT." As discussed above, a MIN operation can be used in lieu of AND. Thus, a MIN(B,C) operation can be used. As discussed above, a DIFF(a,b) operation can be used in lieu of "AND NOT." Thus, a DIFF(A, MIN(B,C)) operation can be used. Note that FIG. 6B depicts operations that correspond to those in Table V for G3.

Figure 6C:
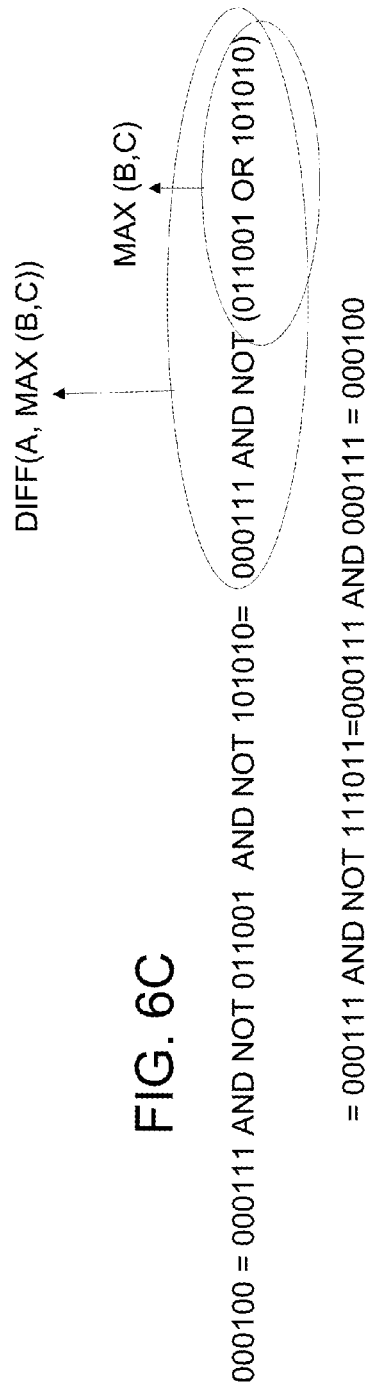

FIG. 6C shows an example for "000100." The example shows a number of equivalent expressions, which are expressed in terms of operators "AND", "OR", as well as "AND NOT." As discussed above, a MAX operation can be used in lieu of an OR operation. Thus, a MAX(B,C) operation can be used, as depicted. As discussed above, a DIFF(a,b) operation can be used in lieu of "AND NOT." Thus, a DIFF(A, MAX(B,C)) operation can be used, as depicted. Note that FIG. 6C depicts operations that correspond to those in Table V for G4.

Similar analysis can be performed to derive the operations in Table V for the other glints. The foregoing demonstrates how N images (corresponding to N binary patterns) can theoretically be used to detect $2^N-2$ unique glint to light source mappings. As noted above, the analysis can be extended to other cases.

In one embodiment, the object 101 can be illuminated with a light source for which it is not desired to map a glint. In the flow of FIG. 6A, this corresponds to the example in which the light source 107 is always on for all binary patterns. For example, light sources L7-L9 in Table II are non-detectable. Note that such a light source 107 is not a "detectable light source." That is to say, steps 622-634 are not used to map glints to that light source 107, which is on for all binary patterns used in steps 606-608. Herein, this is referred to as a "non-detectable" light source 107.

These non-detectable light sources 107 can be turned off when capturing the All On image. Note that it is not required to have these non-detectable light sources 107 off when capturing the All On image. In the event that these non-detectable light sources 107 are kept off when capturing the All On image, then an additional refinement may be made to determining the glint free image. This refinement can be made at any time in the process of FIG. 6A. For example, it could be made prior to initializing the glint free image (step 612), after the glint free image has been updated with each Sequence Image (after step 614 has been performed for the final time), or in-between these two events.

Figure 7:
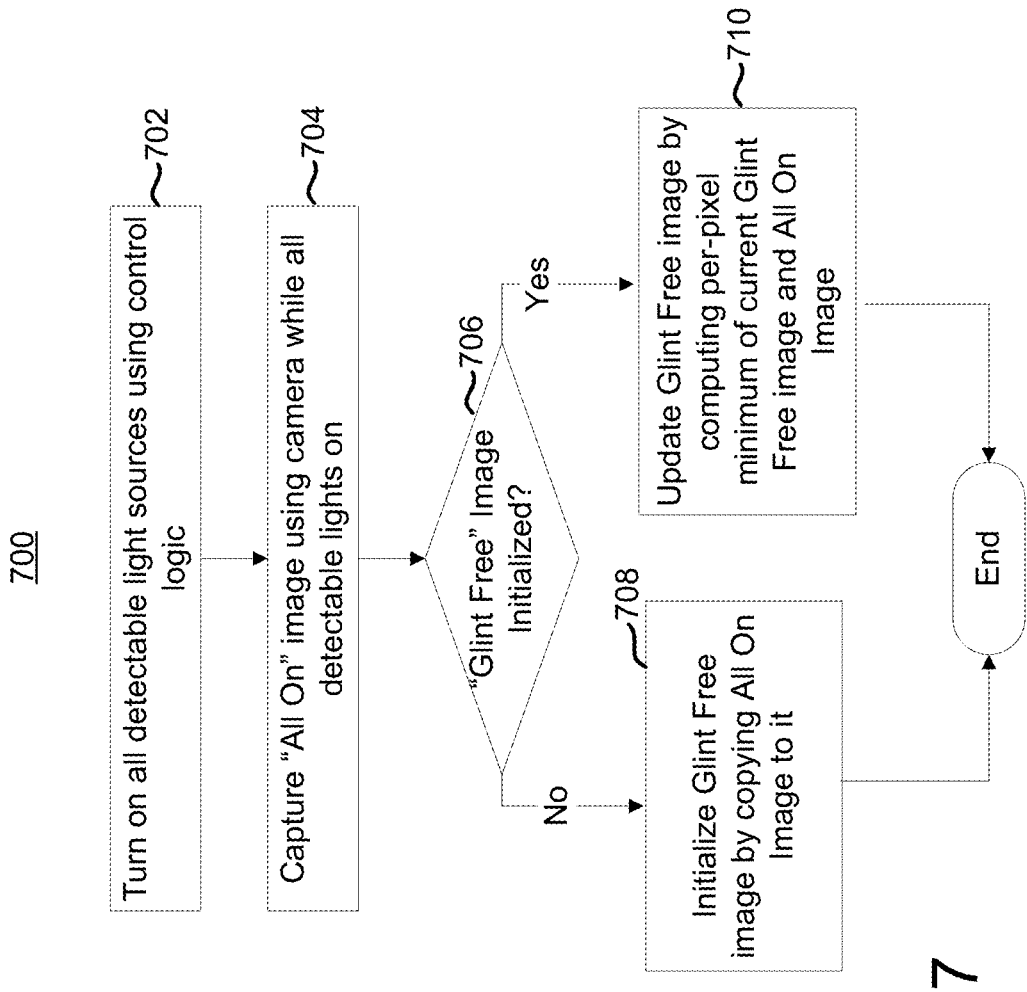
FIG. 7 is a flowchart of a process of refining a glint free image.

FIG. 7 is a flowchart of a process 700 of refining the glint free image. This may be used in connection with producing the glint free image in FIG. 6A, as just described. Control circuitry 103 may perform this process. In step 702, all detectable light sources 107 are turned on. Using the example from Table II, lights L1-L6 are turned on, with lights L7-L9 kept off. In step 704, an All On image is captured using the camera 107 while the detectable light sources 107 are turned on.

In step 706, a determination is made whether the glint free image has already been initialized. This initialization occurs in step 612 of FIG. 6A, in one embodiment. If not, then the glint free image is initialized by copying the All On image to it.

On the other hand, if the glint free image has been initialized (step 706=yes), then control passes to step 710. In step 710, the present glint free image is updated by computing the per-pixel minimum of the present glint free image and the All On image. Further processing of the glint free image is described in FIG. 6A.

Figure 8:
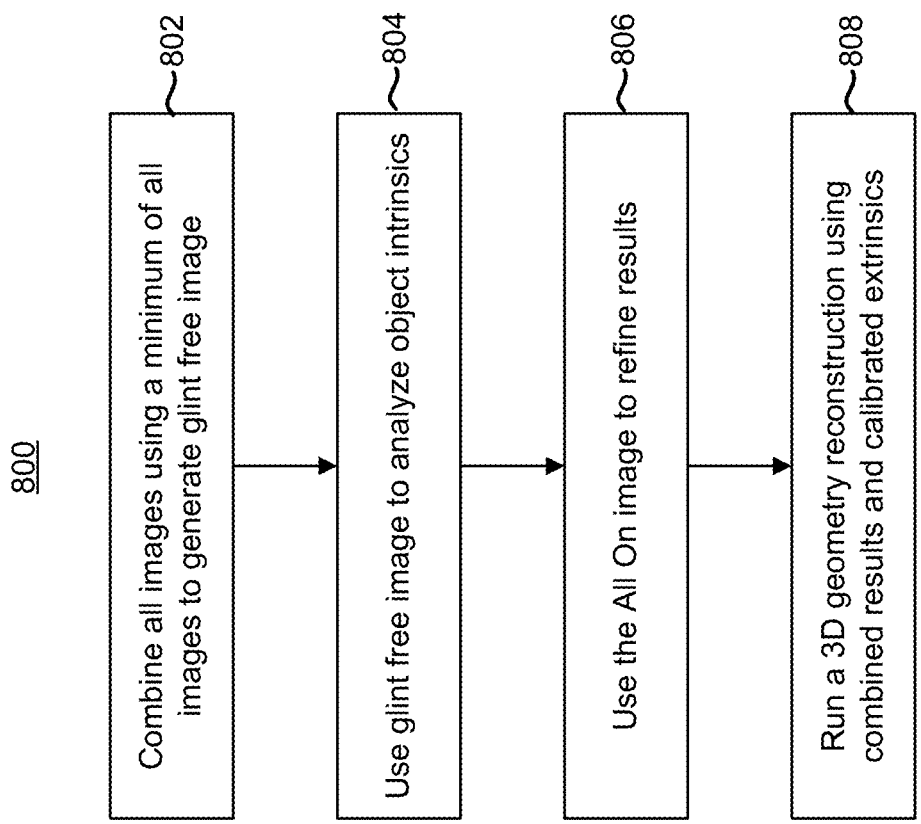
FIG. 8 is a flowchart of a process of further processing that can be performed in addition to mapping glints to light sources.

FIG. 8 is a flowchart of a process 800 of further processing that can be performed in addition to mapping glints to light sources 107. In step 802, the captured images are combined using a minimum of all images to generate a glint free image. Examples of step 802 were previously described in connection with process 500 and process 600. For example, step 516 repeatedly computes a per-pixel minimum as new Glint L images are captured. In process 600, step 614 repeatedly computes a per-pixel minimum as new Sequence S images are captured.

In step 802, the glint free image is used to analyze the object 101. The glint free image has the advantage of good illumination without light reflection, allowing better input data for analysis of intrinsics, such as pupil location. Pupil location is a key input element for 3D eye gaze reconstruction. The glint free image may be used for other purposes such as biometric mapping of the iris.

In step 806, the All On image is used to refine results. This has been previously discussed as the spatial synchronization/refinement. This may be used in connection with process 201, 500 or process 600.

In step 808, 3D geometry reconstruction is performed using the results and calibrated extrinsics. One example of 3D geometry reconstruction is to determine 3D geometry of a person's eye and to determine an eye gaze. This is further described below. This may be based on calibrated extrinsics, which are data that is not necessarily derived from the images.

An example was previously described of mapping glints to six light sources 107. For example, in steps 606-608, three different binary patterns may be used, as described in Table II. In some cases, it may be desirable to map glints to additional light sources. By using four different binary patterns/images in steps 606-608, glints can be mapped to up to 14 light sources 107. However, the computational complexity may increase significantly when using four binary patterns.

One embodiment includes a hybrid approach. For example, the technique of using three patterns to map glints to six light sources 107 can be combined with using two patterns to map glints to two light sources 107. This results in being able to use four patterns to map glints to eight light sources 107.

As another example, the technique of using three patterns to map glints to six light sources 107 can be combined with using three patterns to map glints to six light sources 107. This results in being able to five patterns to map glints to 12 light sources 107.

The former example will now be discussed of using four patterns to map glints to eight light sources. Table VI shows the four binary patterns that can be used. Each binary pattern is described by the column labeled Image A, B, C, or D. Light sources L1-L8 are the detectable light sources in this example. Light sources L9-L12 are not required. These are the non-detectable light sources, which may be used for additional illumination. Note that for each Image, eight lights are on, resulting in uniform illumination intensity.

TABLE VI

| LS  | Image A | Image B | Image C | Image D | All On |
|-----|---------|---------|---------|---------|--------|
| L1  | 0       | 0       | 1       | 1       | 1      |
| L2  | 0       | 1       | 0       | 0       | 1      |
| L3  | 0       | 1       | 1       | 0       | 1      |
| L4  | 1       | 0       | 0       | 0       | 1      |
| L5  | 1       | 0       | 1       | 1       | 1      |
| L6  | 1       | 1       | 0       | 0       | 1      |
| L7  | 1       | 1       | 1       | 0       | 1      |
| L8  | 0       | 0       | 0       | 1       | 1      |
| L9  | 1       | 1       | 1       | 1       | 0      |
| L10 | 1       | 1       | 1       | 1       | 0      |
| L11 | 1       | 1       | 1       | 1       | 0      |
| L12 | 1       | 1       | 1       | 1       | 0      |

The glint candidates may be found as depicted in Table VII. That is, Table VII describes suitable operations that may be applied to the captured images to map glints to light sources. Note that this table reflects a combination of techniques for using three binary patterns to map glints to six light sources and using two binary patterns to map glints to two light sources.

TABLE VII

| Glint   |                   |
|---------|-------------------|
| Glint 1 | Diff(C, Max(A, B))|
| Glint 2 | Diff(B, Max(A, C))|
| Glint 3 | Diff(Min(B, C), A)|
| Glint 4 | Diff(A, Max(B, C))|
| Glint 5 | Diff(Min(A, C), B |
| Glint 6 | Diff(Min(A, B), C)|
| Glint 7 | Diff(C, D)        |
| Glint 8 | Diff(D, C)        |

One possible use case for the glints is in eye gaze reconstruction. The following is an overview of how this may be achieved. A fixed setup with the camera 105 and a number of light sources 107 is set up and calibrated. Calibration involves determining absolute or relative locations of light sources 107 (e.g., LEDs) and camera projection point. In some cases, objects 101 within the field of view may need to be calibrated as well. Relative positioning may work in place of absolute positioning depending on the full system geometry.

The system can be used to reconstruct the eye gaze of a subject. Due to expected high-speed motion of the human eye, a high-speed camera and precise control circuitry is generally used. Once the subject is within the view of the system, the control circuitry 103 engages light sources 107 in a predetermined pattern, and takes multiple images in rapid sequence, each image corresponding to a different binary pattern.

The captured images are delivered to a processor for analysis, and the processor uses algorithms described herein to detect and match each glint to its light source 107. Glint locations and mappings are used in consequent 3D analysis and eye gaze reconstruction.

Figure 9:
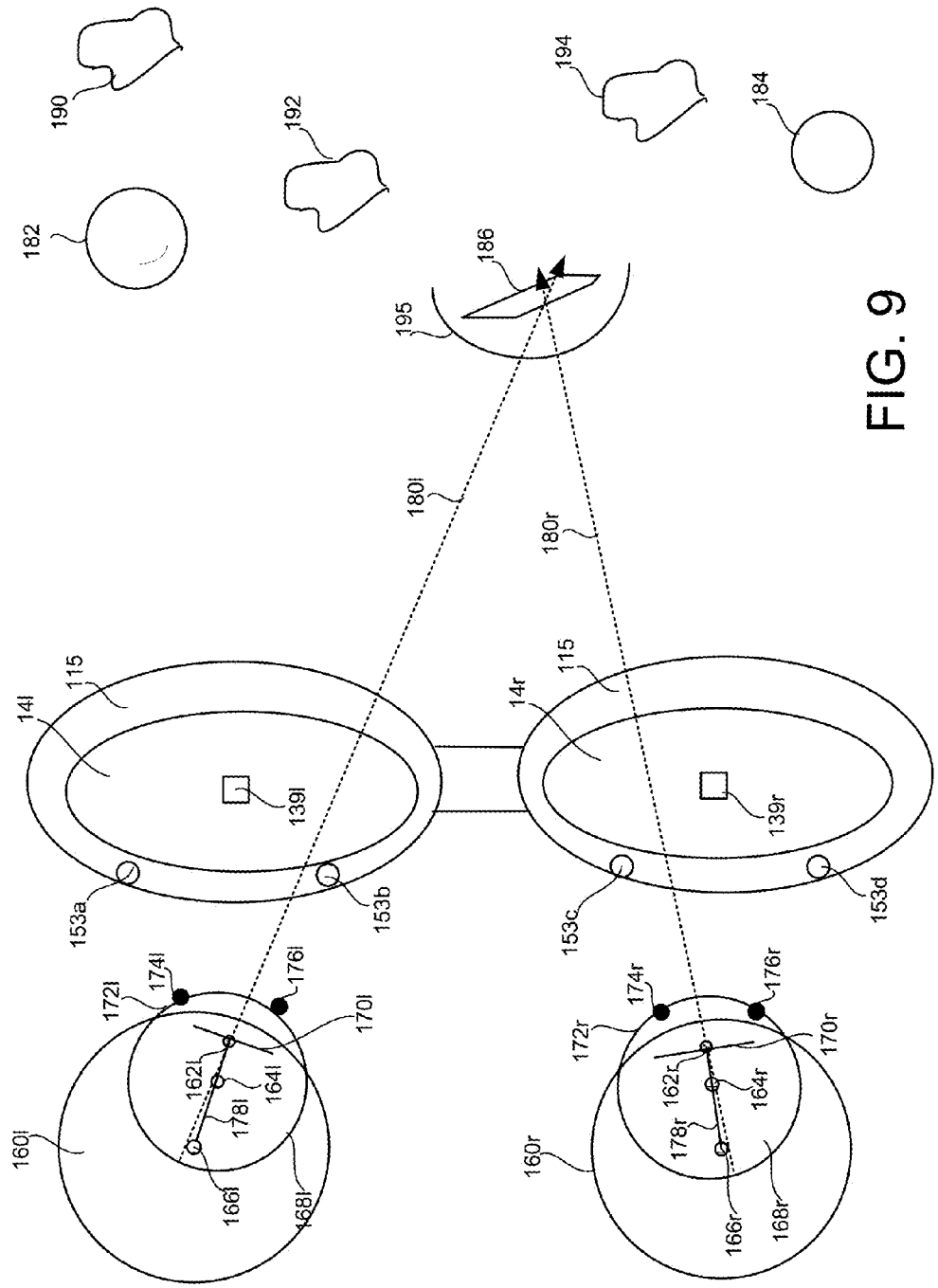
FIG. 9 is a top view illustrating examples of gaze vectors intersecting at a point of gaze where a person's eyes are focused.

FIG. 9 shows additional details of determining an eye gaze. FIG. 9 is a top view illustrating examples of gaze vectors intersecting at a point of gaze where a person's eyes are focused. A model of the eye 160*l*, 160*r* is illustrated for each eye based on the Gullstrand schematic eye model. For each eye, an eyeball 160 is modeled as a sphere with a center of rotation 166 and includes a cornea 168 modeled as a sphere too and having a center 164. The cornea rotates with the eyeball, and the center 166 of rotation of the eyeball may be treated as a fixed point. The cornea covers an iris 170 with a pupil 162 at its center. In this example, on the surface 172 of the respective cornea are glints 174 and 176.

The axis 178 formed from the center of rotation 166 through the cornea center 164 to the pupil 162 is the optical axis of the eye. A gaze vector 180 is sometimes referred to as the line of sight or visual axis which extends from the fovea through the center of the pupil 162. The fovea is a small area of about 1.2 degrees located in the retina. The angular offset between the optical axis computed in the embodiment of FIG. 9 and the visual axes has horizontal and vertical components. The horizontal component is up to 5 degrees from the optical axis, and the vertical component is between 2 and 3 degrees. In many embodiments, the optical axis is determined and a small correction determined through user calibration is applied to obtain the visual axis which is selected as the gaze vector. For each user, a small virtual object may be displayed by the display device at each of a number of predetermined positions at different horizontal and vertical positions. An optical axis may be computed for during display of the object at each position, and a ray modeled as extending from the position into the user eye. An offset angle with horizontal and vertical components may be determined based on how the optical axis must be moved to align with the modeled ray. From the different positions, an average offset angle with horizontal or vertical components can be selected as the small correction to be applied to each computed optical axis. In some embodiments, only a horizontal component is used for the offset angle correction.

In the illustrated embodiment of FIG. 9, a sensor detection area 139 is aligned with the optical axis of each display optical system 14 within an eyeglass frame 115. The respective image sensor in this example is a camera capable of capturing image data representing glints 174*l* and 176*l* generated respectively by illuminators 153*a* and 153*b* on the left side of the frame 115 and data representing glints 174*r* and 176*r* generated respectively by illuminators 153*c* and 153*d*.

Through the display optical systems, 14*l* and 14*r* in the eyeglass frame 115, the user's field of view includes both real objects 190, 192 and 194 and virtual objects 182, 184, and 186. In this example, the cornea 168*l* of the left eye is rotated to the right or towards the user's nose, and the cornea 168*r* of the right eye is rotated to the left or towards the user's nose. Both pupils are gazing at a virtual object 186. Gaze vectors 180*l* and 180*r* from each eye enter the Panum's fusional region 195 in which virtual object 186 is located. The Panum's fusional region is the area of single vision in a binocular viewing system like that of human vision. The intersection of the gaze vectors 180*l* and 180*r* indicates that the user is looking at virtual object 186.

For a see-through mixed reality display device, the gaze vectors are determined to identify a point of gaze in a three-dimensional (3D) user field of view which includes both real objects, typically not under computer control, and virtual objects generated by an application. The gaze vectors may intersect at an object 10 feet away or at a distance effectively at infinity. The following figures briefly discuss embodiments for determining a 3D user field of view.

References to front facing image data are referring to image data from one or more front facing camera like camera 113 in FIG. 3A. In these embodiments, the field of view of the front facing camera 113 approximates the user field of view as the camera is located at a relatively small offset from the optical axis 142 of each display optical system 14. The offset may be taken into account in the image data.

Figure 10:
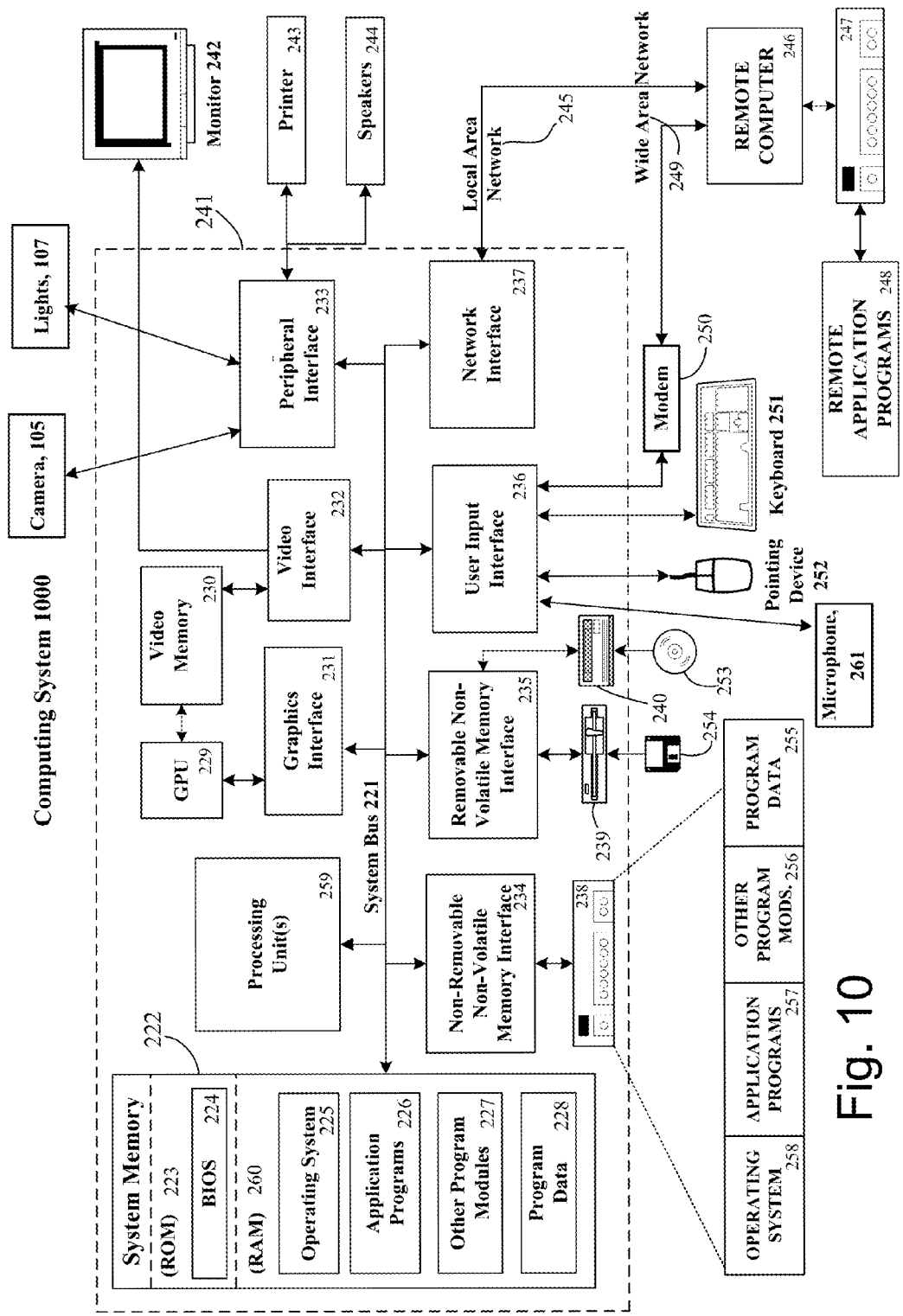
FIG. 10 is a block diagram of one embodiment of a computing system that can be used to implement embodiments.

FIG. 10 depicts an example block diagram of a computing device. The computing device may be used to implement all or a portion of control circuitry 103, and/or processor 4. The computing device may be used to perform all or a portion of various algorithms described herein, including but not limited to, processes 201, 500, 600, 700, and 800. Instructions that execute on the processing unit 259 may control the camera 105 and the light sources 107, via peripheral interface 233.

The computing system 1000 comprises a computer 241, which typically includes a variety of tangible computer-readable storage media. This can be any available media that can be accessed by computer and includes both volatile and nonvolatile media, removable and non-removable media. The system memory 222 includes computer storage media in the form of volatile and/or nonvolatile memory such as read only memory (ROM) 223 and random access memory (RAM) 260. A basic input/output system 224 (BIOS), containing the basic routines that help to transfer information between elements within computer, such as during start-up, is typically stored in ROM 223. RAM 260 typically contains data and/or program modules that are immediately accessible to and/or presently being operated on by processing unit 259. A graphics interface 231 communicates with a GPU 229. Operating system 225, application programs 226, other program modules 227, and program data 228 are also provided.

The computer may also include other removable/non-removable, volatile/nonvolatile computer storage media, e.g., a hard disk drive 238 that reads from or writes to non-removable, nonvolatile magnetic media, a magnetic disk drive 239 that reads from or writes to a removable, nonvolatile magnetic disk 254, and an optical disk drive 240 that reads from or writes to a removable, nonvolatile optical disk 253 such as a CD ROM or other optical media. Other removable/non-removable, volatile/nonvolatile tangible computer-readable storage media that can be used in the exemplary operating environment include, but are not limited to, magnetic tape cassettes, flash memory cards, digital versatile disks, digital video tape, solid state RAM, solid state ROM, and the like. The hard disk drive 238 is typically connected to the system bus 221 through an non-removable memory interface such as interface 234, and magnetic disk drive 239 and optical disk drive 240 are typically connected to the system bus 221 by a removable memory interface, such as interface 235.

The drives and their associated computer storage media provide storage of computer-readable instructions, data structures, program modules and other data for the computer. For example, hard disk drive 238 is depicted as storing operating system 258, application programs 257, other program modules 256, and program data 255. Note that these components can either be the same as or different from operating system 225, application programs 226, other program modules 227, and program data 228. Operating system 258, application programs 257, other program modules 256, and program data 255 are given different numbers here to depict that, at a minimum, they are different copies. A user may enter commands and information into the computer through input devices such as a keyboard 251 and pointing device 252, commonly referred to as a mouse, trackball or touch pad. Other input devices may include a microphone 261, joystick, game pad, satellite dish, scanner, or the like. These and other input devices are often connected to the processing unit 259 through a user input interface 236 that is coupled to the system bus, but may be connected by other interface and bus structures, such as a parallel port, game port or a universal serial bus (USB). A monitor 242 or other type of display device is also connected to the system bus 221 via an interface, such as a video interface 232. In addition to the monitor, computers may also include other peripheral devices such as speakers 244 and printer 243, which may be connected through a peripheral interface 233.

The computer may operate in a networked environment using logical connections to one or more remote computers, such as a remote computer 246. The remote computer 246 may be a personal computer, a server, a router, a network PC, a peer device or other common network node, and typically includes many or all of the elements described above relative to the computer, although only a memory storage device 247 has been depicted. The logical connections include a local area network (LAN) 245 and a wide area network (WAN) 249, but may also include other networks. Such networking environments are commonplace in offices, enterprise-wide computer networks, intranets and the Internet.

When used in a LAN networking environment, the computer is connected to the LAN 245 through a network interface or adapter 237. When used in a WAN networking environment, the computer typically includes a modem 250 or other means for establishing communications over the WAN 249, such as the Internet. The modem 250, which may be internal or external, may be connected to the system bus 221 via the user input interface 236, or other appropriate mechanism. In a networked environment, program modules depicted relative to the computer, or portions thereof, may be stored in the remote memory storage device. Remote application programs 248 reside on memory device 247. It will be appreciated that the network connections shown are exemplary and other means of establishing a communications link between the computers may be used.

The computing system can include a tangible computer-readable storage device or apparatus having computer-readable software embodied thereon for programming at least one processor to perform methods as described herein. The tangible computer-readable storage device can include, e.g., one or more of components 222, 234, 235, 230, 253 and 254. Further, one or more processors of the computing system can provide processor-implemented methods as described herein. The GPU 229 and the processing unit 259 are examples of processors.

The example computer systems illustrated in the figures include examples of computer readable storage media. Computer readable storage media are also processor readable storage media. Such media may include volatile and nonvolatile, removable and non-removable media implemented in any method or technology for storage of information such as computer readable instructions, data structures, program modules or other data. Computer storage media includes, but is not limited to, RAM, ROM, EEPROM, cache, flash memory or other memory technology, CD-ROM, digital versatile disks (DVD) or other optical disk storage, memory sticks or cards, magnetic cassettes, magnetic tape, a media drive, a hard disk, magnetic disk storage or other magnetic storage devices, or any other medium which can be used to store the desired information and which can accessed by a computer.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method comprising:
 illuminating an object with patterns of a plurality of light sources, the patterns including a first pattern in which a first light source of the light sources is on and a second pattern in which the first light source is off;

capturing a plurality of images of the object at a camera while illuminating the object with corresponding ones of the patterns, wherein each of the light sources is off for at least one of the plurality of images and on for at least one of the plurality of images;

determining a min image that is a per-pixel minimum of all of the images for which the first light source is on;

determining a max image that is a per-pixel maximum of all of the images for which the first light source is off;

computing a difference image that is the per-pixel unsigned saturated subtract operation of the max image subtracted from the min image;

analyzing glints in the captured plurality of images; and mapping a glint in the difference image to the first light source.

2. The method of claim 1, wherein the capturing and the analyzing comprise:

capturing a first image of the plurality of images with all of the plurality of light sources on;

capturing a second image of the plurality of images with a second light source off and the rest of the plurality of light sources on;

comparing the second image with the first image to determine which glint is missing in the second image; and further comprising:

mapping the missing glint to the second light source that was off when the second image was captured.

3. The method of claim 2, wherein the capturing a plurality of images comprises capturing additional images with exactly one of the plurality of light sources off and the rest of the plurality of light sources on; wherein the analyzing comprises comparing each additional image with the first image to determine a glint that is missing in each additional image; and further comprising mapping the glint that is missing in each of the additional images to the light source that is off for each additional image.

4. The method of claim 1, wherein the capturing comprises:

capturing an image while all of the plurality of light sources are illuminating the object;

capturing a plurality of additional images while ones of the patterns are illuminating the object, each of the additional images is captured with exactly one of the plurality of light sources off and the rest of the plurality of light sources on;

establishing a working image as the image captured while all of the plurality of light sources are illuminating the object;

for each of the plurality of light sources, updating the working image based on a per-pixel minimum between the working image and the image for which exactly one of the light sources is off and the rest of the light sources are on, resulting in a final working image; and establishing the final working image as a glint free image.

5. The method of claim 1, further comprising:

for each of the plurality of light sources in addition to the first light source:

repeating the determining a min image, the determining a max image, the computing a difference image, and the mapping a glint in the difference image to the respective light source.

6. The method of claim 5, wherein glints are mapped to their respective light sources using fewer captured images than light sources.

7. The method of claim 1, further comprising establishing a working image as a first of the captured images;

for remaining ones of the plurality of captured images, updating the working image based on a per-pixel minimum between the working image and the image, resulting in a final working image; and establishing the final working image as a glint free image.

8. A system comprising:

a plurality of light sources;

a camera; and logic in communication with the plurality of light sources and the camera, the logic is configured to:

control the light sources to illuminate an object with patterns of the plurality of light sources, the patterns including a first pattern in which a first light source of the light sources is on and a second pattern in which the first light source is off, wherein each of the light sources is off for at least one of the patterns and on for at least one of the patterns;

capture a plurality of images of the object at the camera while illuminating the object with corresponding different ones of the patterns, wherein each of the light sources is off for at least one of the plurality of images and on for at least one of the plurality of images;

determine a min image that is a per-pixel minimum of all of the images for which the first light source is on;

determine a max image that is a per-pixel maximum of all of the images for which the first light source is off;

compute a difference image that is the per-pixel unsigned saturated subtract operation of the max image subtracted from the min image;

analyze glints in the captured plurality of images as a result of illuminating the object with the patterns;

map a glint in the difference image to the first light source; and perform a per-pixel minimum of the plurality of captured images to generate a glint free image.

9. The system of claim 8, wherein the logic being configured to capture and to analyze comprises the logic being configured to:

capture a first image of the plurality of images with all of the plurality of light sources on;

capture a second image of the plurality of images with a second light source off and the rest of the plurality of light sources on;

generate a per-pixel difference image (Diff(A,B) =Max(0, A-B), where A is the first image and B is the second image; and map a glint in the per-pixel difference image to the second light source that was off when the second image was captured.

10. The system of claim 9, wherein the logic is further configured to:

capture a plurality of additional images while other ones of the patterns are illuminating the object, each of the additional images is captured with exactly one of the plurality of light sources off and the rest of the plurality of light sources on;

for each of the additional images, generate a per-pixel difference image (Diff(A,B) =Max(0, A-B), where A is the first image and B is the additional image; and for each of the additional images, map a glint in the corresponding per-pixel difference image to the light source that is off for the additional image.

11. The system of claim 8, wherein, for each of the plurality of light sources in addition to the first light source, the logic is further configured to:
   determine a min image, determine a max image, compute a difference image, and map a glint in the difference image to the respective light source.

12. The method of claim 1, further comprising:
   based on analyzing the glints, mapping a glint in the captured plurality of images to a light source of the plurality of light sources that is responsible for the glint.

13. The system of claim 8, wherein the logic is further configured to: map a glint in the captured plurality of images to a light source of the plurality of light sources that is responsible for the glint.

14. The system of claim 8, further comprising:
   a see-through, near-eye display in communication with the logic.

15. A system comprising:
   a plurality of light sources;
   a camera; and
   logic in communication with the plurality of light sources and the camera, wherein the logic is configured to:
      control the light sources to illuminate an object with patterns of the plurality of light sources, the patterns including a first pattern in which all of the plurality of light sources are on and a second pattern in which a first light source is off and the rest of the plurality of light sources are on;
      capture a first image with all of the plurality of light sources on;
      capture a second image with the first light source off and the rest of the plurality of light sources on;
      generate a per-pixel difference image (Diff(A,B) =Max(0, A-B), wherein A is the first image and B is the second image; and
      map a glint in the per-pixel difference image to the first light source that was off when the second image was captured.

16. The system of claim 15, wherein the logic being configured to capture, to generate, and to map comprises the logic being configured to:
   capture a plurality of additional images while other ones of the patterns are illuminating the object, each of the additional images is captured with exactly one of the plurality of light sources off and the rest of the plurality of light sources on;
   for each of the additional images, generate a per-pixel difference image (Diff(A,B) =Max(0, A-B), where A is the first image and B is the additional image; and
   for each of the additional images, map a glint in the corresponding per-pixel difference image to the light source that is off for the additional image.

17. A system comprising:
   a plurality of light sources;
   a camera; and
   logic in communication with the plurality of light sources and the camera, wherein the logic is configured to:
      control the light sources to illuminate an object with patterns of the plurality of light sources, the patterns including a first pattern in which a first light source of the light sources is on and a second pattern in which the first light source is off, wherein each of the light sources is off for at least one of the patterns and on for at least one of the patterns;
      capture a plurality of images of the object at the camera while illuminating the object with corresponding different ones of the patterns;
      determine a min image that is a per-pixel minimum of all of the images for which the first light source is on;
      determine a max image that is a per-pixel maximum of all of the images for which the first light source is off;
      compute a difference image that is the per-pixel unsigned saturated subtract operation of the max image subtracted from the min image;
      analyze glints in the captured plurality of images as a result of illuminating the object with the patterns; and
      map a glint in the difference image to the first light source.

18. The system of claim 17, wherein, for each of the plurality of light sources in addition to the first light source, the logic is further configured to:
   determine a min image, determine a max image, compute a difference image, and map a glint in the difference image to the respective light source.

* * * * *